United States Patent
Hahn et al.

(10) Patent No.: US 6,330,735 B1
(45) Date of Patent: Dec. 18, 2001

(54) APPARATUS AND PROCESS FOR FORMING A LAID FIBROUS WEB WITH ENHANCED BASIS WEIGHT CAPABILITY

(75) Inventors: John Timothy Hahn, Merrill; Michael Barth Venturino, Appleton; Bradley John Berken, Greenville; Raymond Gerard St. Louis, Fremont; Paul Joseph Datta, Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/785,959

(22) Filed: Feb. 16, 2001

(51) Int. Cl.$^7$ ................................................ D01G 25/00
(52) U.S. Cl. ........................... 19/296; 19/301; 403/294; 425/80.1
(58) Field of Search .............. 19/148, 296, 301, 19/302, 304, 307, 308; 29/895.2, 895.3; 198/397.03; 209/284, 288, 296, 297, 405, 406, 397, 399, 684, 686; 264/112, 121; 403/292, 294, 401; 425/80.1, 81.1

(56) References Cited

U.S. PATENT DOCUMENTS

| | | |
|---|---|---|
| Re. 29,789 | 10/1978 | Kolbach . |
| Re. 31,775 | 12/1984 | Persson . |
| 3,518,726 | 7/1970 | Banks . |
| 3,717,905 | 2/1973 | Furbeck . |
| 3,748,693 | 7/1973 | Jespersen . |
| 3,846,871 | 11/1974 | Kolbach . |
| 3,939,240 * | 2/1976 | Savich ................... 264/121 |
| 3,973,291 | 8/1976 | Kolbach . |
| 4,005,957 * | 2/1977 | Savich ................... 264/112 |
| 4,016,628 | 4/1977 | Kolbach . |
| 4,333,463 | 6/1982 | Holtman . |
| 4,388,056 * | 6/1983 | Lee et al. ............... 425/80.1 |
| 4,449,979 | 5/1984 | Holtman . |
| 4,592,708 * | 6/1986 | Feist et al. ............. 425/80.1 |
| 4,666,647 * | 5/1987 | Enloe et al. ............. 19/308 |
| 4,674,966 | 6/1987 | Johnson et al. . |
| 4,761,258 * | 8/1988 | Enloe ...................... 264/121 |
| 4,834,735 | 5/1989 | Alemany et al. . |
| 4,859,388 | 8/1989 | Peterson et al. . |
| 4,888,231 * | 12/1989 | Angstadt ................. 19/302 |
| 4,892,470 * | 1/1990 | Farrington et al. .... 425/80.1 |
| 4,915,897 | 4/1990 | Farrington et al. . |
| 4,921,659 | 5/1990 | Marshall et al. . |
| 4,927,582 * | 5/1990 | Bryson ................... 264/121 |
| 4,995,141 * | 2/1991 | Gould .................... 19/148 |
| 5,004,579 * | 4/1991 | Wislinski et al. ........ 264/112 |
| 5,047,023 | 9/1991 | Berg . |
| 5,064,484 * | 11/1991 | Craig et al. ............. 425/80.1 |
| 5,076,774 | 12/1991 | Farrington et al. . |
| 5,226,991 | 7/1993 | Svaighert . |
| 5,302,100 | 4/1994 | Scheu et al. . |
| 5,447,677 * | 9/1995 | Griffoul et al. ......... 425/80.1 |
| 5,466,409 * | 11/1995 | Partridge et al. ....... 425/81.1 |
| 5,494,622 * | 2/1996 | Heath et al. ............. 264/121 |
| 5,540,872 * | 7/1996 | Ulman .................... 264/121 |
| 5,575,874 * | 11/1996 | Griesbach, III et al. .. 19/301 |
| 5,866,173 * | 2/1999 | Reiter et al. ............ 425/80.1 |
| 5,885,623 * | 3/1999 | Edvardsson et al. .... 425/81.1 |
| 5,893,197 * | 4/1999 | Vartiainen .............. 19/301 |
| 6,098,249 * | 8/2000 | Toney et al. ............ 19/296 |

* cited by examiner

Primary Examiner—John J. Calvert
Assistant Examiner—Gary L. Welch
(74) Attorney, Agent, or Firm—Paul Yee

(57) ABSTRACT

A method and apparatus for forming an airlaid fibrous web on a moving surface can include a contoured foraminous member (62) having a first side portion (66), a laterally opposed second side portion (68), and a depth contour. A longitudinally extending, first side-masking member (52) can be located superjacent the first side portion (66) of the foraminous member (62), and can have a first inboard side wall surface (70). At least a second, separately provided, longitudinally extending, side-masking member (53) can be located superjacent the second side portion (68) of the foraminous member (62), and can have a second inboard side wall surface (72). Either or both of the first and second side-masking members (52, 54) are at least laterally movable relative to the foraminous member (62). A releasable attachment system (74) can selectively hold at least the first side-masking member (52) at a substantially fixed position relative to the foraminous member (62).

21 Claims, 15 Drawing Sheets

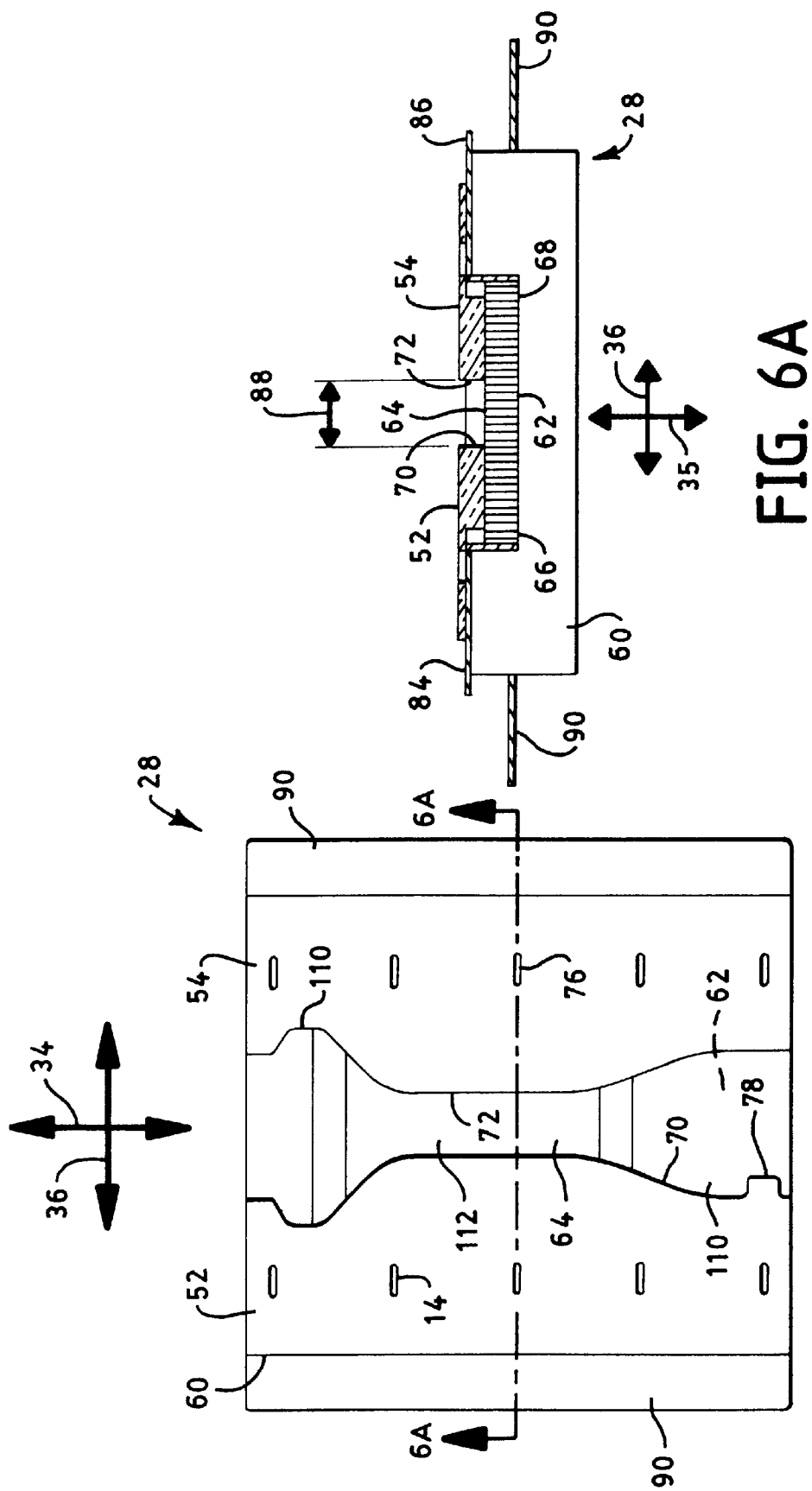

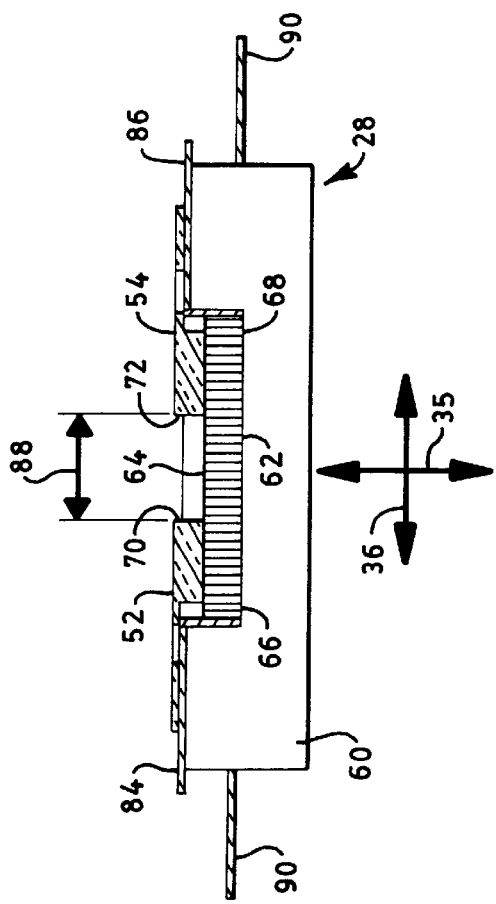
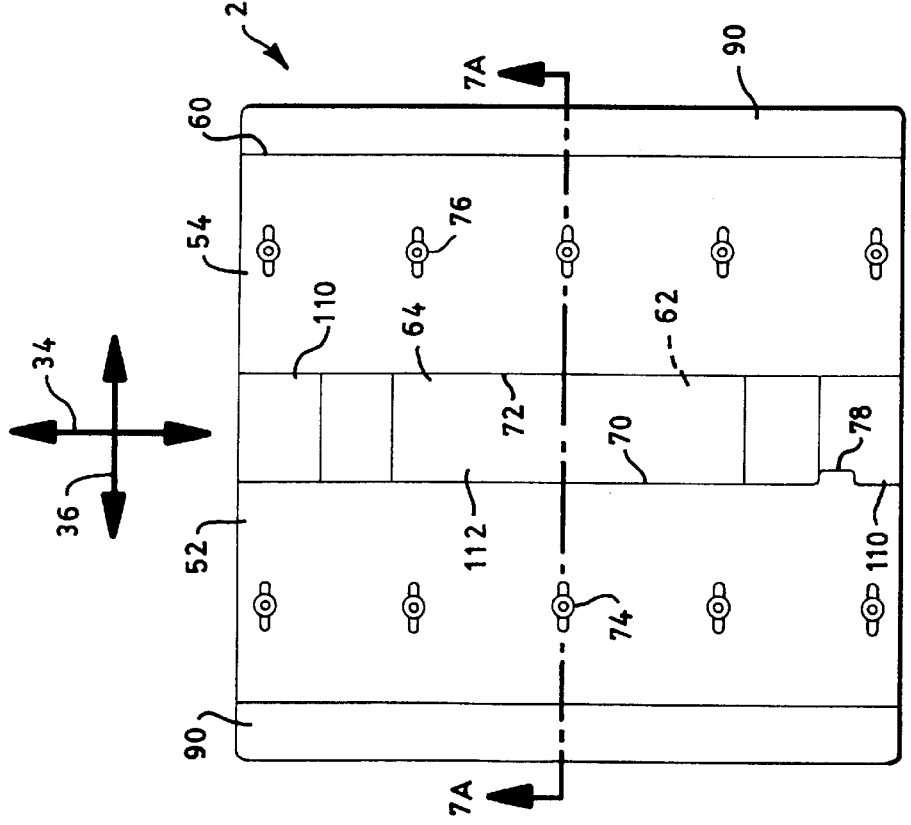

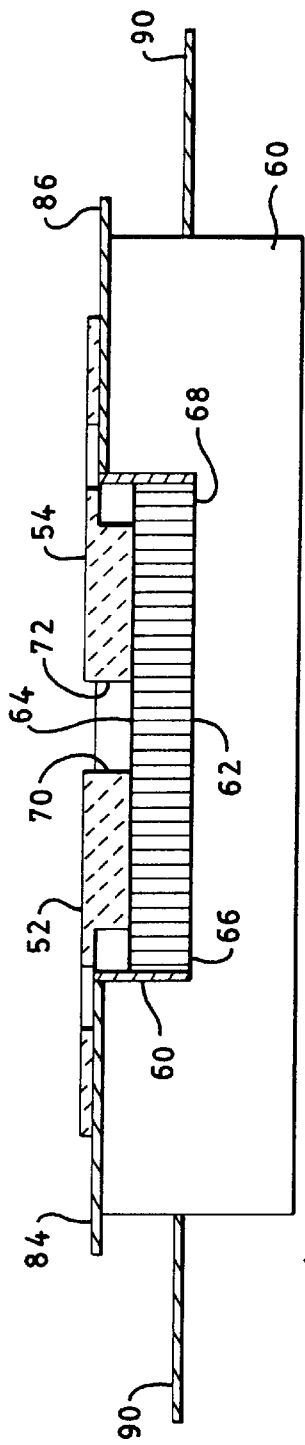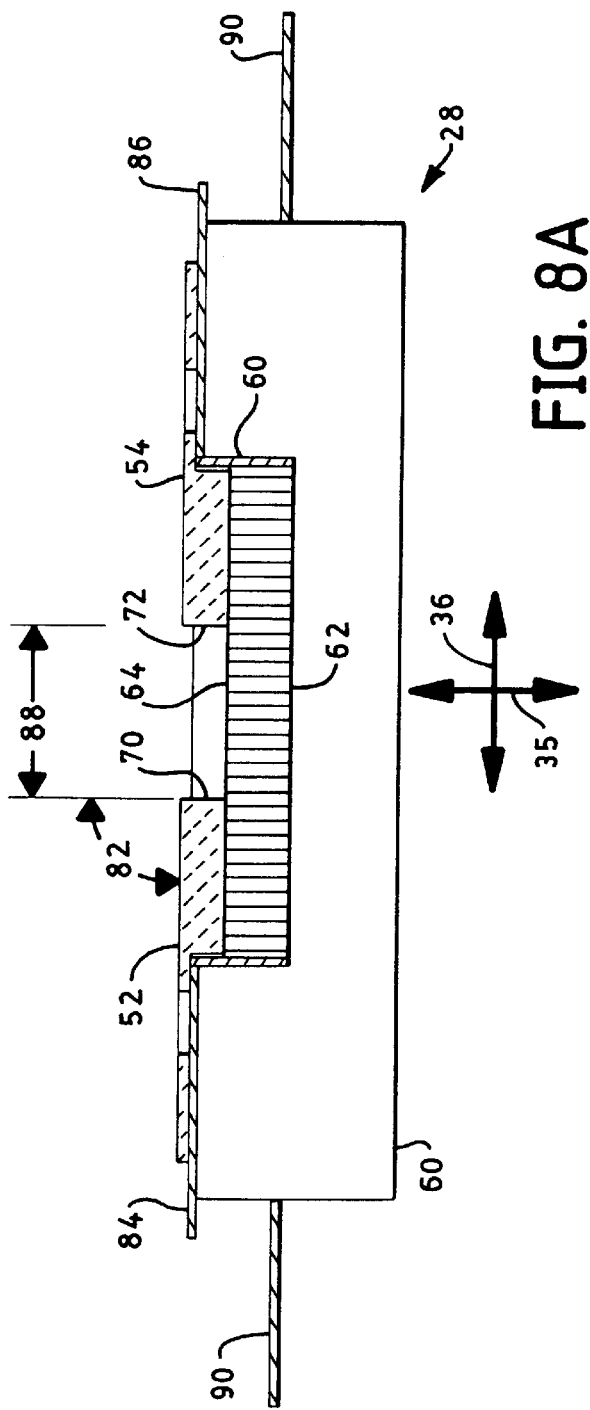

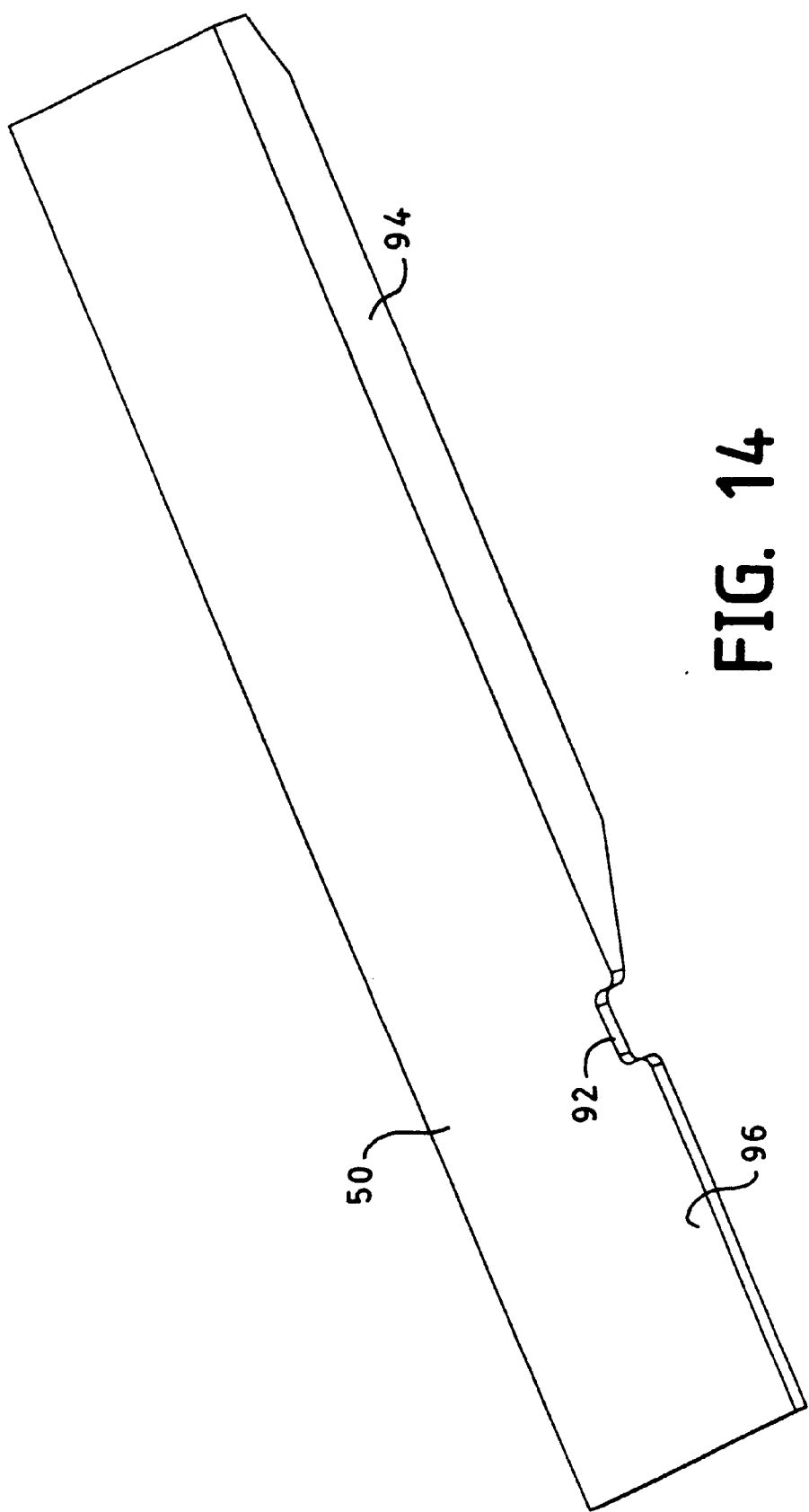

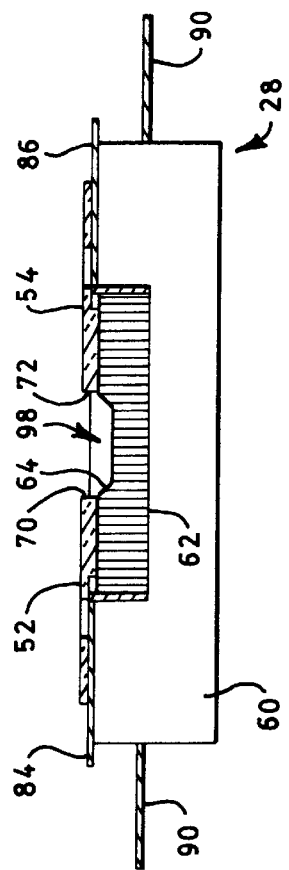
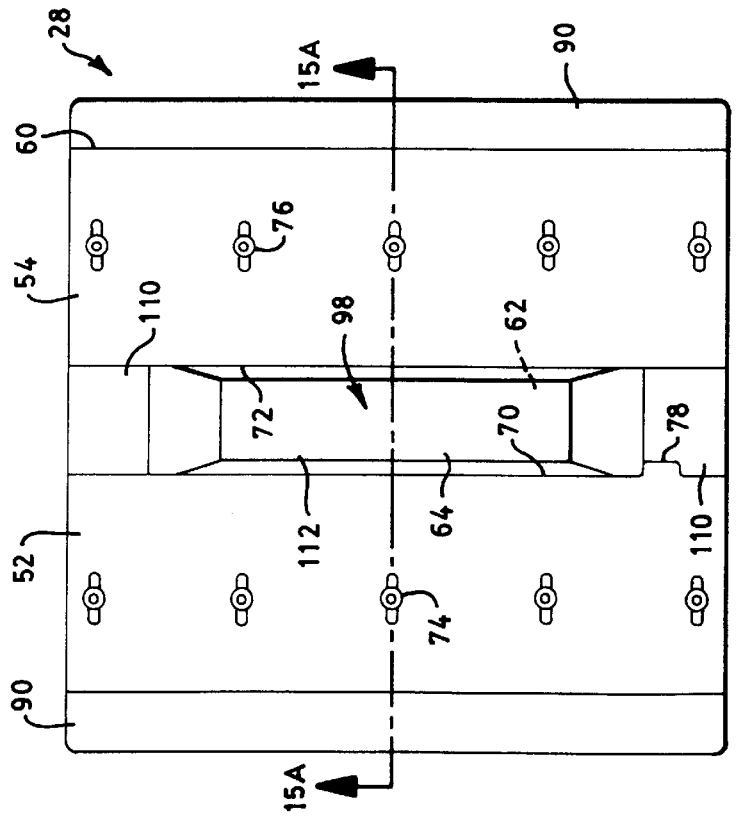

APPARATUS AND PROCESS FOR FORMING A LAID FIBROUS WEB WITH ENHANCED BASIS WEIGHT CAPABILITY

FIELD OF THE INVENTION

This invention generally relates to apparatus and method for forming an airlaid fibrous article. The fibrous article can be a fibrous web which can be employed to produce an absorbent pad for applications such as disposable diapers, child's training pants, feminine care articles, incontinence articles, and the like.

BACKGROUND OF THE INVENTION

In the general practice of forming fibrous web materials, such as laid fibrous articles, it has been common to utilize a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous web.

The forming surfaces utilized in such systems have been constructed with a wire or screen grid and can typically employ a pneumatic flow mechanism, such as vacuum suction apparatus, to define a differential pressure zone on the forming surface and impose a pressure differential thereon. The pressure difference has typically provided an airflow through the openings or perforations in the screen or grid of the forming surface. The use of vacuum suction to draw the air-entrained fiber stream onto the forming surfae, and pass the airflow through the forming surface has been employed in high-speed commercial operations.

The prior practice of forming airlaid fibrous webs has also employed various mechanisms to produce gradations in basis weight along the fibrous webs. For example, the mechanisms have been employed produce gradations of basis weight along a longitudinal direction of the formed web, i.e., in the direction of movement of the fibrous web through the forming process. Conventional mechanisms have also been employed for providing basis weight variations along a transverse, cross-direction of the formed web.

Conventional vacuum-deposition systems, such as those described above, have continued to exhibit various shortcomings. For example, with the conventional devices, it has been difficult to maintain a well mixed, superabsorbent distribution in narrow regions of the fibrous web. The conventional systems can excessively funnel the superabsorbent particles toward the cross-directional center of the forming surface. The conventional techniques have also produced an excessively non-uniform distribution of basis weight of fibrous material along the cross-direction in the narrow regions of the fibrous web. Additionally, the conventional techniques have not provided a sufficiently convenient method or apparatus for changing the dimensions of the formed fibrous web. Where the formed fibrous web includes an interconnected plurality of web segments, it has been difficult to adjust the dimensions of the desired web segments without a significant reconstruction of the forming surface. Changes to the dimensions of the formed fibrous web have required the procurement, storage and maintenance of multiple sets of forming screens and introduced excessive downtime and change over costs. Accordingly, it would be a substantial advance in the art to provide a method and apparatus which can provide a more efficient removal of the formed web from the forming surface, and can better provide an adjusting of the dimensions of the intended web segments to more efficiently form components for articles of various, different sizes.

BRIEF DESCRIPTION OF THE INVENTION

The present invention provides a distinctive method and apparatus for forming an airlaid fibrous article. An apparatus for forming an airlaid fibrous web on a moving surface has a longitudinal direction, a lateral cross-direction, and a depth-wise, z-direction. The apparatus can include a contoured foraminous member having a first side portion, a laterally opposed second side portion, and a depth contour formed into a thickness of the foraminous member. A longitudinally extending, first side-masking member can be located superjacent the first side portion of the foraminous member, and can have a first inboard side wall surface. In a particular feature, the first side-masking member can be at least laterally movable relative to the foraminous member. At least a second, separately provided, longitudinally extending, side-masking member can be located superjacent the second side portion of the foraminous member, and can have a second inboard side wall surface. In a particular aspect, the second side-masking member can be at least laterally movable relative to the foraminous member. In another feature, a first releasable attachment system can selectively hold at least the first side-masking member at a substantially fixed position relative to the foraminous member during a movement of the foraminous member along the longitudinal direction.

In a process or method aspect, the invention can include a moving of a selected surface, and a providing of a foraminous member. The foraminous member can be provided with a first side portion, a laterally opposed second side portion, and a depth contour formed into a thickness of the foraminous member. A longitudinally extending, first side-masking member can be located superjacent the first side portion of the foraminous member, and can be provided with a first inboard side wall surface. In a particular feature, the first side-masking member can be configured to be at least laterally movable relative to the foraminous member. At least a second, separately provided, longitudinally extending, side-masking member can be located superjacent the second side portion of the foraminous member, and can be provided with a second inboard side wall surface. In a particular aspect, the second side-masking member can be configured to be at least laterally movable relative to the foraminous member. Another feature can include a providing of a first releasable attachment system which can selectively hold at least the first side-masking member at a substantially fixed position relative to the foraminous member during a movement of the foraminous member along the longitudinal direction.

In its various aspects and features, the present invention can more effectively help to increase the quantity of absorbent material distributed into desired higher-basis-weight sections of the forming surface. Additionally, the technique of the invention can better provide a desired cross-directional distribution of superabsorbent material in the appointed high-basis-weight sections of the forming surface. The releasable attachment system employed with the present invention can improve the ability to adjust the method and apparatus to accommodate the formation of fibrous webs with different dimensions, particularly different cross-directional dimensions. The various features and aspects of the invention can also help reduce the fabrication costs of the forming surface and can help facilitate the cleaning and maintenance of the forming surface.

BRIEF DESCRIPTION OF THE DRAWINGS

The invention will be more fully understood and further advantages will become apparent when reference is made to the following detailed description of the invention and to the drawings in which:

FIG. 6 shows a schematic, top view of representative portion of a foraminous forming surface that has side-masking members with non-parallel, laterally-shaped and transversely undulating, inboard side walls;

FIG. 6A representatively shows a transverse, cross-sectional view taken along line 6A—6A of the arrangement illustrated in FIG. 6;

FIG. 7 representatively shows a schematic top view of a portion of a foraminous forming surface that includes side-masking members having inboard side walls that are substantially straight and parallel to each other along the circumference of the forming drum;

FIG. 7A representatively shows a transverse, cross-sectional view taken along line 7A—7A of the arrangement illustrated in FIG. 7;

FIG. 8 representatively shows a schematic, transverse, cross-sectional view of a foraminous forming surface wherein the side-masking members have been arranged relatively closer to each other to provide a fibrous web having a relatively narrower cross-directional width;

FIG. 8A representatively shows a schematic, transverse, cross-sectional view of a foraminous forming surface wherein the side-masking members have been arranged relatively farther from each other to provide a fibrous web having a relatively wider cross-directional width;

FIG. 14 representatively shows a schematic, perspective view of a representative fibrous web segment which can be formed by employing the method and apparatus of the invention;

FIG. 15 representatively shows a schematic top view of a portion of a foraminous forming surface having a foraminous member which includes a formed depression that can assist in the production of a high-basis-weight region of the formed web or pad;

FIG. 15A representatively shows a transverse, cross-sectional view taken along line 15A—15A of the arrangement illustrated in FIG. 15.

DETAILED DESCRIPTION OF THE INVENTION

It should be noted that, when employed in the present disclosure, the terms "comprises", "comprising" and other derivatives from the root term "comprise" are intended to be openended terms that specify the presence of any stated features, elements, integers, steps, or components, and are not intended to preclude the presence or addition of one or more other features, elements, integers, steps, components, or groups thereof.

Figure 1:
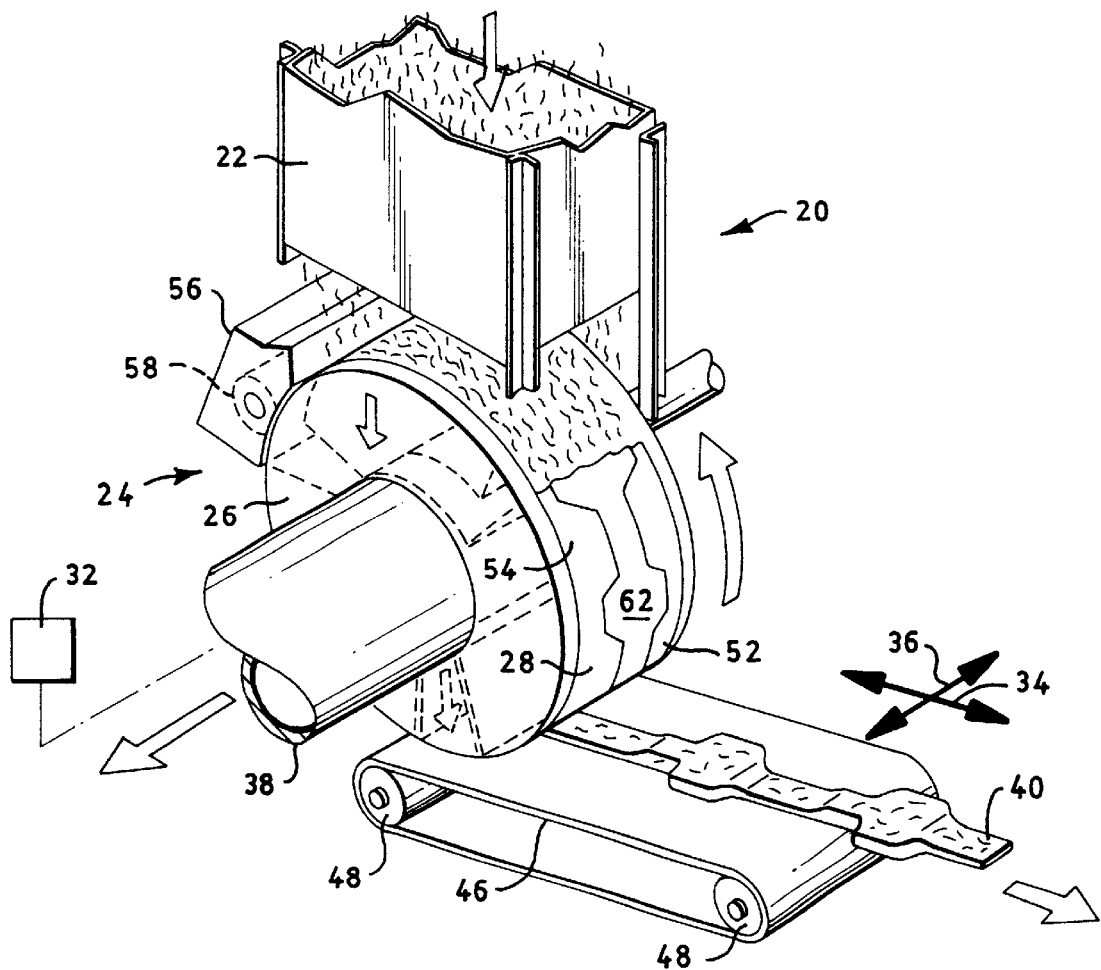
FIG. 1 shows a schematic, partially cut-away, perspective view of a representative method and apparatus that can incorporate the present invention to provide a fibrous web having transversely shaped side margins.

With reference to FIGS. 1 and 6A, the process and apparatus 20 of the invention can have a lengthwise, machine-direction 34 which extends longitudinally, a lateral cross-direction 36 which extends transversely, and an appointed z-direction 35. For the purposes of the present disclosure, the machine-direction 34 is the direction along which a particular component or material is transported length-wise along and through a particular, local position of the apparatus and method. The cross-direction 36 lies generally within the plane of the material being transported through the process, and is aligned perpendicular to the local machine-direction 34. The z-direction is aligned substantially perpendicular to both the machine-direction 34 and the cross-direction 36, and extends generally along a depthwise, thickness dimension.

As illustrated in FIGS. 1, 6 and 6A, a representative apparatus and method for forming an airlaid fibrous web 40 on a moving surface has a longitudinal, machine-direction 34, a lateral cross-direction 36, and a depth-wise, z-direction 35 (e.g. FIG. 6A). The moving surface can provide a selected forming surface 28, and can include a contoured foraminous member 62 having a first side portion 66, a laterally opposed second side portion 68, and a depth-wise contour formed into a thickness of the foraminous member 62. A longitudinally extending, first side-masking member 52 can be located superjacent the first side portion 66 of the foraminous member 62, and can have a first inboard side wall surface 70, With a particular aspect, the first inboard side wall can have a selected contour shape. In the shown arrangement, the first side-masking member 52 can be configured to overlie the first side portion 66 of the foraminous member. The first side-masking member 52 can be at least laterally movable relative to the foraminous member 62, and can be a separately provided member. At least a second, separately provided, longitudinally extending, side-masking member 54 can be located superjacent the second side portion 68 of the foraminous member 62, and can have a second inboard side wall surface 72. With a particular aspect, the second inboard side wall can have a selected contour shape. As representatively shown, the second side-masking member 54 can be configured to overlie the second side portion 68 of the foraminous member, and the second side-masking member 54 can be at least laterally movable relative to the foraminous member 62. The second side-masking member 54 can also be at least laterally movable relative to the first side-masking member 52. A first releasable attachment system 74 can selectively hold at least the first side-masking member 52 at a substantially fixed position relative to the foraminous member 62 during a movement of the foraminous member 62 along the longitudinal direction 34. In an additional aspect, the method and apparatus of the invention can further include a second releasable attachment system 76 for selectively holding the second side-masking member 54 at a substantially fixed position relative to the foraminous member 62 during the moving of the foraminous member along the longitudinal, machine-direction 34.

A method for forming an airlaid fibrous web can include a longitudinal moving of a selected surface. The selected surface can include a contoured foraminous member 62 having a first side portion 66, a laterally opposed second side portion 68 and a depth contour formed into a thickness of the foraminous member 62. In a particular aspect, a longitudinally extending first side-masking member 52, such as provided by a first ring member, can be located at a position which is superjacent the first side portion 66 of the foraminous member 62. The first side-masking member or ring member 52 can be provided with a first inboard side wall surface 70, and the first side-masking member or ring member 52 can be configured to be at least laterally movable relative to the oraminous member 62. Additionally, the first inboard side wall can be configured with a selected contour shape. In another feature, at least a second, separately provided, longitudinally extending, side-masking member or ring member 54 can be located at a position which is superjacent the second side portion 68 of the foraminous member 62. The second side-masking member or ring member 54 can be provided with a second inboard side wall surface 72, and the second side-masking member or ring member 54 can be configured to be at least laterally movable relative to the foraminous member 62. In a particular feature, the second inboard side wall can be configured with a selected contour shape. Additionally, the second side-masking member can be configured to be at least laterally movable relative to the first side-masking member or ring member 52. In another aspect, the method can include a selective holding of at least the first side-masking members 52 with a releasable attachment system at a substantially fixed position relative to the foraminous member 62 during the longitudinal moving of the foraminous member. For example, the method can include a providing of a first releasable attachment system 74. In a further aspect, the method may further include a holding of the second side-masking members 54 with a releasable attachment system at a substantially fixed position relative to the foraminous member, and may include a providing of a second releasable attachment mechanism 76. Other aspects and features are set forth in the present disclosure.

By incorporating its various aspects and features, the method and apparatus of the present invention can more effectively distribute the fibrous material with a desired basis weight distribution along the cross-direction in the narrow, crotch regions of the fibrous web 40. In particular arrangements, the cross-directional basis weight distribution can be more uniformly provided. Additionally, the invention can help to increase the quantity of absorbent material distributed into the appointed higher-basis-weight sections of the forming surface 28. The invention can also help to better maintain a well mixed superabsorbent distribution in the narrow, crotch regions of the fibrous web 40. The technique of the invention can more effectively reduce an undesired funneling of superabsorbent material toward the cross-directional center of the forming surface 28. Additionally, the technique of the invention can improve the cross-directional distribution of superabsorbent material in the appointed high-basis-weight sections of the forming surface 28. The releasable attachment system employed with the present invention can improve the ability to adjust the method and apparatus to accommodate the formation of fibrous webs with different dimensions, particularly different cross-directional dimensions. The various features and aspects of the invention can also reduce the fabrication costs of the forming surface 28 and can facilitate the cleaning and maintenance of the forming surface.

Figure 2:
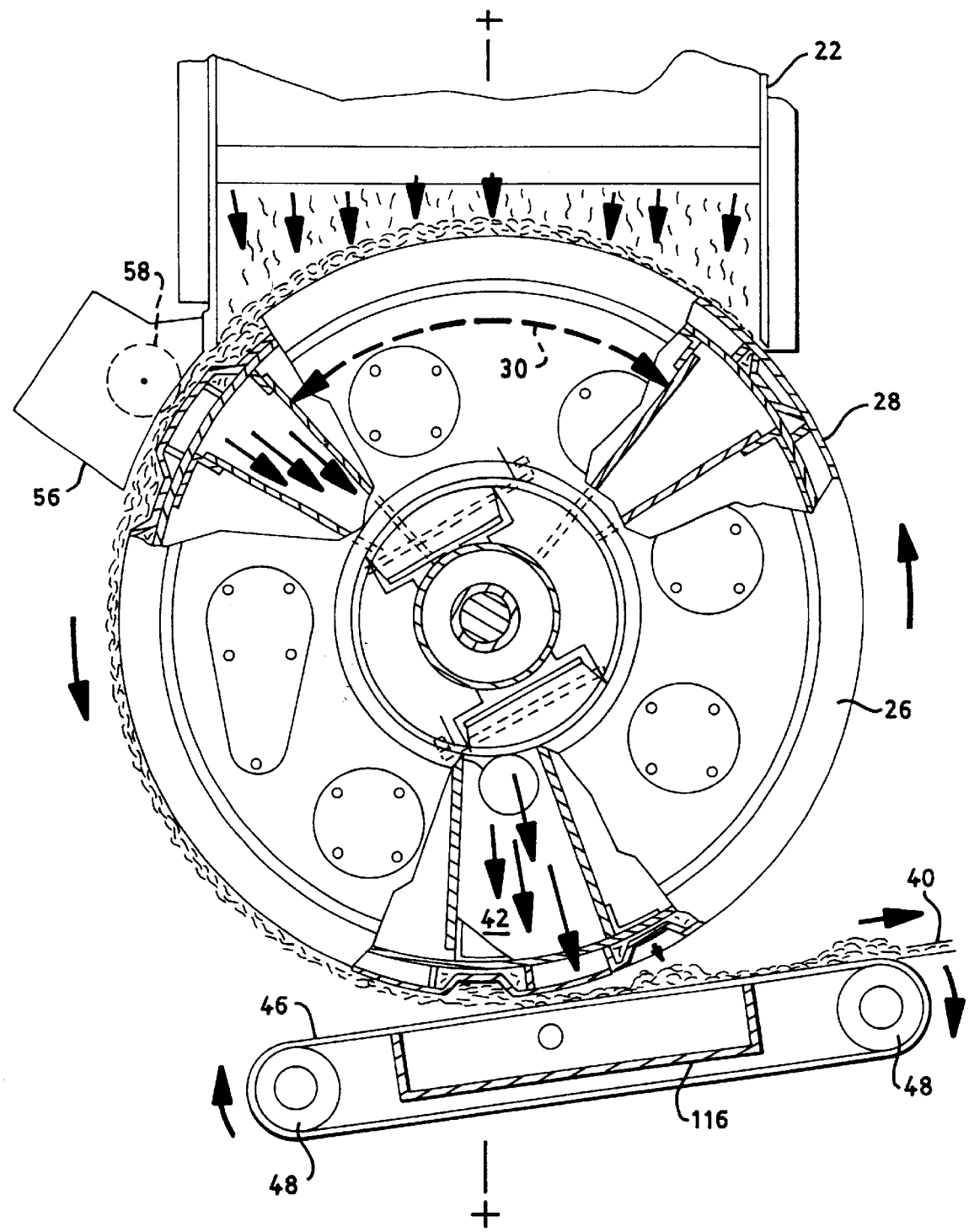
FIG. 2 shows a, partially cut-away, side view of a representative method and apparatus that can incorporate the present invention.
Figure 3:
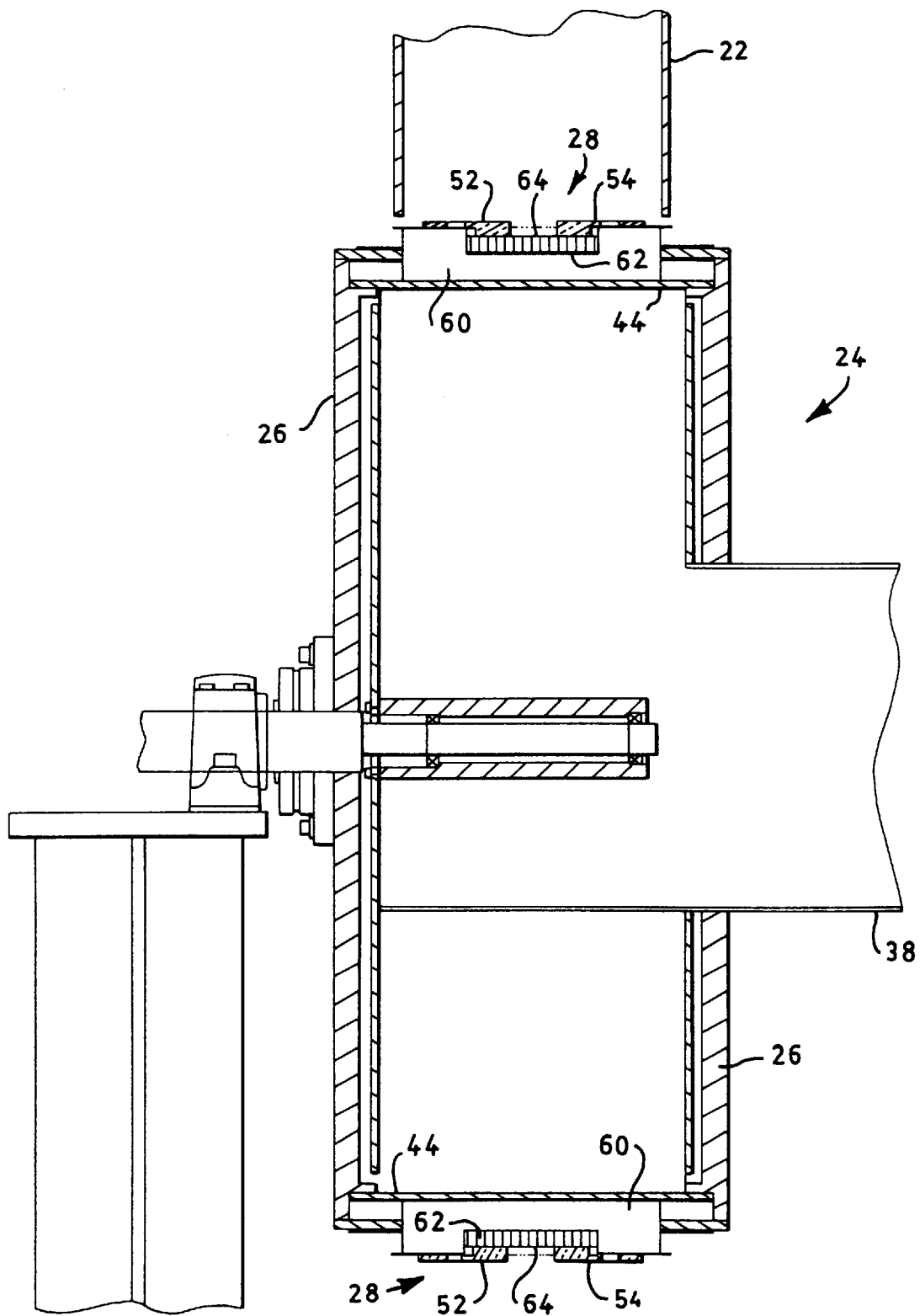
FIG. 3 shows a, partially sectioned, end view of a representative method and apparatus that can incorporate the present invention.

With reference to FIGS. 1, 2 and 3, the selected fibrous material can be introduced into the system as air-entrained fibers in a stream flowing in the direction toward an operative forming surface. The fibers may suitably be derived from a batt of cellulosic fibers (e.g., wood pulp fibers) or other source of natural or synthetic fibers, which has been subjected to a fiberization treatment, in a manner well known in the art, to provide an operative quantity of individual, loose fibers. For example, a hammer mill or other conventional fiberizer may be employed. Particles or fibers of superabsorbent material may also be introduced into the forming chamber 22 by employing conventional mechanisms, such as pipes, channels, spreaders, nozzles and the like, as well as combinations thereof. Superabsorbent materials are well known in the art, and are readily available from various suppliers. For example, FAVOR 880 superabsorbent is available from Stockhausen, Inc., a business having offices located in Greensboro, N.C., U.S.A.; and DOW 2035 is available from Dow Chemical Company, a business having offices located in Midland, Mich., U.S.A. The fibers and particles may be entrained in any suitable gaseous medium, and references herein to air as being the entraining medium should be understood to be a general reference which encompasses any other operative entrainment gas.

The stream of air-entrained fibers and particles can pass through a forming chamber 22 to a forming drum system 24. The forming chamber can serve to direct and concentrate the air-entrained fibers and particles, and to provide a desired velocity profile in the air-entrained stream of fibers and particles. The forming chamber is typically supported by suitable structural members, which together form a support frame for the forming chamber. The frame may be anchored and/or joined to other suitable structural components, as necessary or desirable.

In a particular configuration, the moving surface employed in the invention can be provided by a forming drum system 24. More particularly, the moving surface can be provided by a peripheral surface region of a rotatable forming drum 26. The forming drum is rotatable in a selected direction of rotation, and can be rotated by employing a drum drive shaft that is operatively joined to any suitable drive mechanism (not shown). For example, the drive mechanism can include an electric or other motor which is directly or indirectly coupled to the drive shaft. While the shown arrangement provides a forming drum that is arranged to rotate in a counter-clockwise direction, it should be readily apparent that the forming drum may alternatively be arranged to rotate in a clockwise direction.

The forming drum can provide a laydown zone 30 which is positioned within the forming chamber 22 and provides a vacuum laydown zone of the foraminous forming surface 28. This vacuum laydown zone constitutes a circumferential, cylindrical surface portion of the rotatable drum 26. An operative pressure differential is imposed on the surface of the vacuum laydown zone under the action of a conventional vacuum generating mechanism 32, such as a vacuum pump, an exhaust blower or other suitable mechanism which can provide a relatively lower pressure under the forming surface 28. The vacuum mechanism can operatively withdraw air from the arcuate segment of the forming drum associated with the vacuum laydown surface through an air discharge duct 38. The foraminous forming surface 28 can include a series of forming sections which are distributed circumferentially along the periphery of the forming drum 26. In desired arrangements, the forming sections can provide a selected repeat pattern that is formed in the fibrous web 40. The repeat pattern can correspond to a desired shape of an individual absorbent pad that is intended for assembly or other placement in a desired absorbent article.

Suitable forming drum systems for producing airlaid fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

Thus, under the influence of the vacuum mechanism 32, a conveying air stream is drawn through the foraminous forming surface 28 into the interior of the forming drum, and is subsequently passed out of the drum through the discharge duct 38. As the air-entrained fibers and particles impinge on the foraminous forming surface 28, the air component thereof is passed through the forming surface and the fibers-particles component is retained on the forming surface to form a nonwoven fibrous web 40 thereon. Subsequently, with the rotation of the drum, the formed web 40 can be removed from the forming surface by the weight of the fibrous web 40, by centrifugal force, and by a positive pressure produced, for example, by a pressurized air flow through a blow-off zone 42. The pressurized air exerts a force directed outwardly through the forming surface. Additionally, the distinctive configurations of the forming surface and associated components, can produce a fibrous web 40 which can be more readily removed from the forming drum 26.

The forming drum of the illustrated configuration can be rotatable about a series of stationary baffles which can present to the foraminous forming surface, a plurality of differential pressure zones. The pressure differentials imposed on the foraminous forming surface 28 can be produced by any conventional, vacuum generating mechanism 32, such as an exhaust fan, which is connected to an is air discharge duct 38 and is operatively joined to the forming drum structure by employing a conventional coupling mechanism. The interior space of the forming drum 26 can includes a high vacuum forming zone which is in the general form of an arcuate segment that is operatively located at the portion of the forming surface 28 that is positioned within the forming chamber 22. In the shown configuration, the high vacuum forming zone is located generally subjacent the forming chamber.

Figure 4:
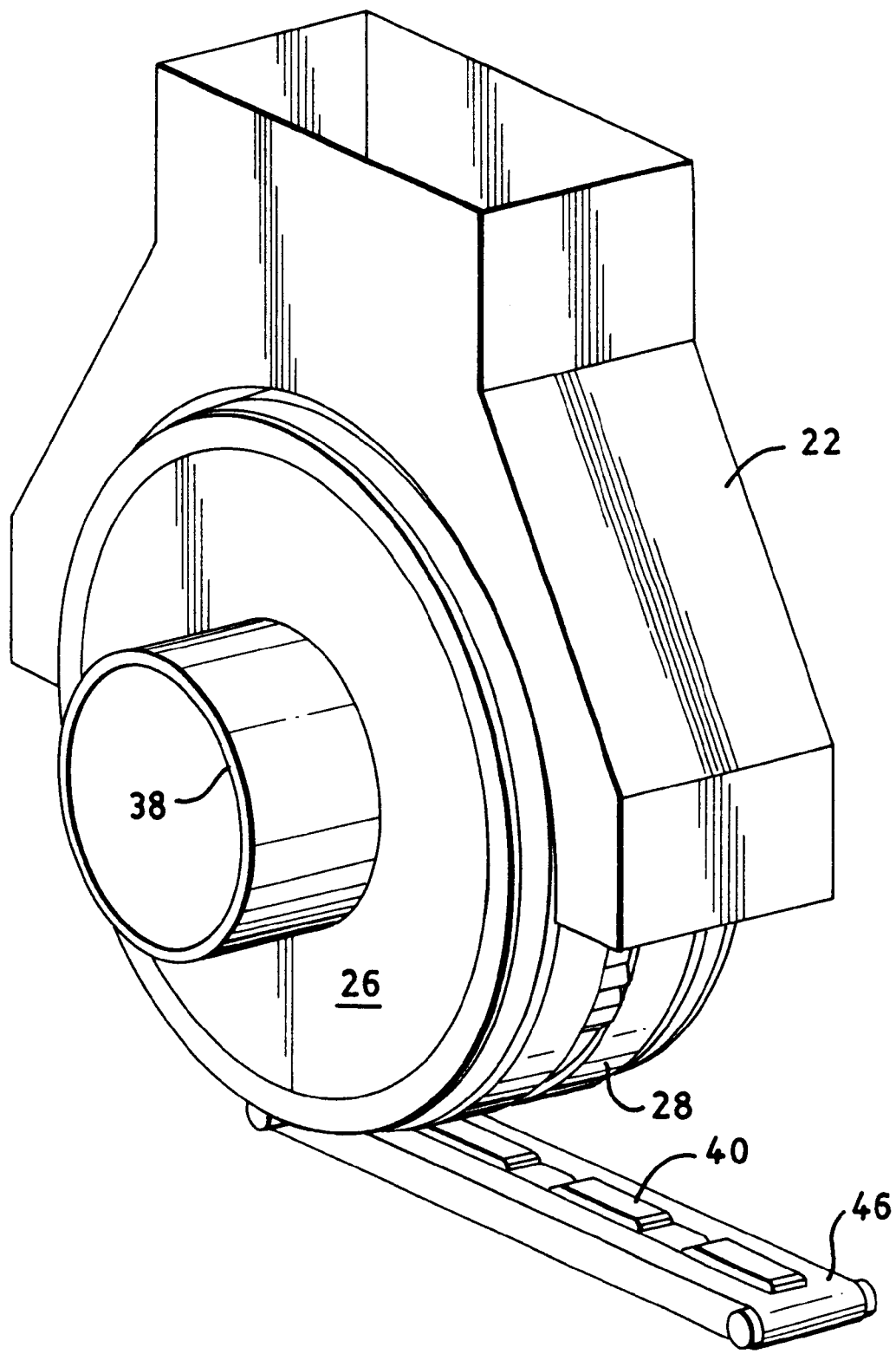
FIG. 4 representatively shows a perspective view of another method and apparatus that can incorporate the present invention to provide a fibrous web having a substantially constant, cross-directional width.
Figure 5:
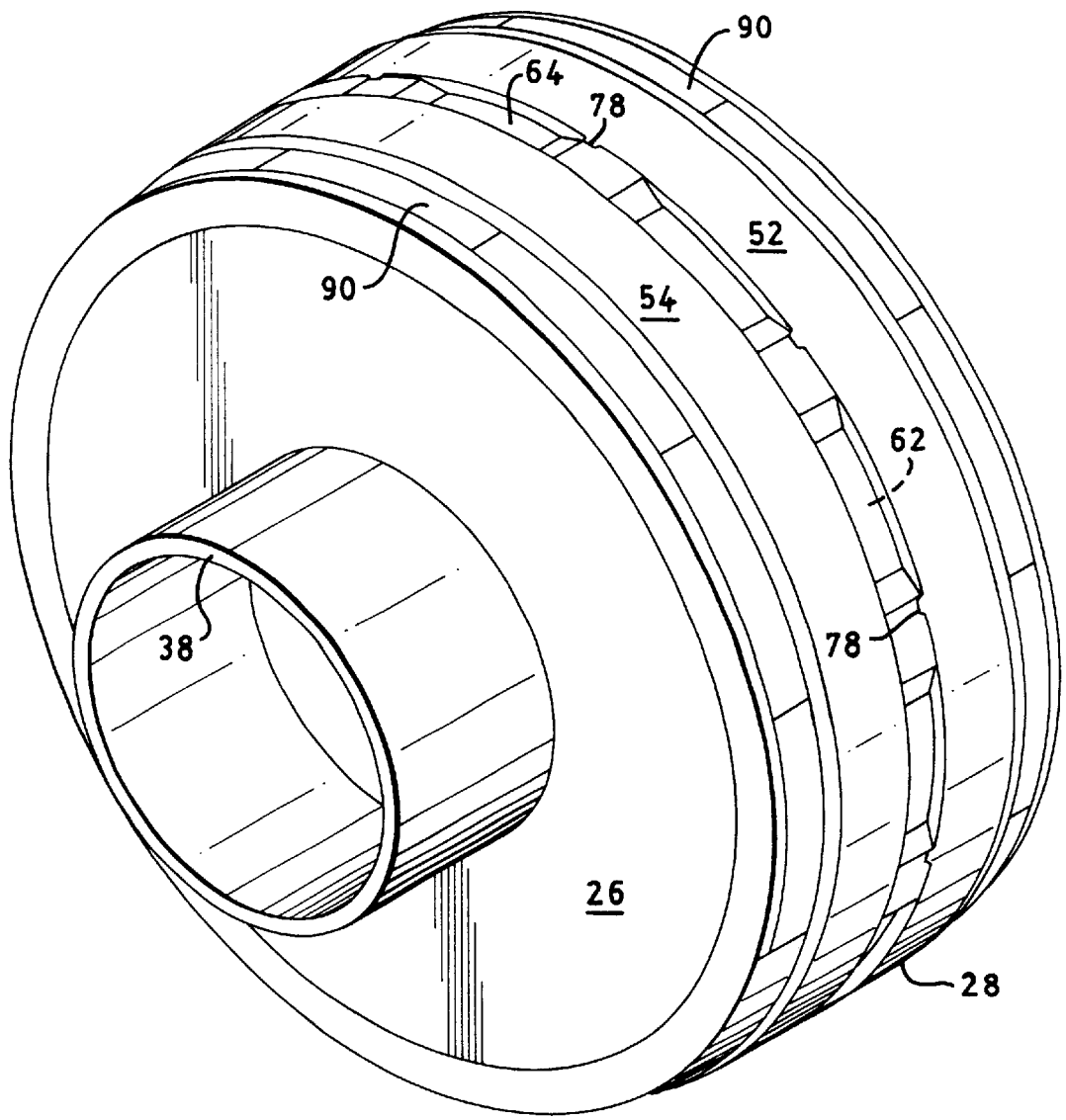
FIG. 5 shows perspective view of a representative forming drum having a plurality of forming surface sections arranged along a periphery of the forming drum to provide a foraminous forming surface.

With reference to FIGS. 1, 4 and 5, the forming surface 28 can be provided along the outer, cylindrical surface of the forming drum 26, and forming surface can include a plurality of concavely contoured forming surface portions that are circumferentially spaced apart along the outer surface of the forming drum.

In operation, the airlaid fibrous web 40 can be formed from the stream of air-entrained fibers (and particles) as the entrainment gas flows through the openings in the foraminous forming surface 28 and into the rotating forming drum 26. The drum rotation can then pass the airlaid fibrous web 40 from the vacuum laydown zone to the scarfing zone where excess thickness of the fibrous web can be trimmed and removed to a predetermined extent. As representatively shown, the fibrous web 40 can be operatively processed by a scarfing roll assembly. The scarfing roll assembly can include scarfing roll chamber 56 which contains a scarfing roll 58 disposed on a suitable shaft member and driven by a suitable drive mechanism (not shown) which may be any conventional mechanism, such as provided by a motor or a coupling by gear or other transmission mechanism to the motor or drive mechanism employed to drive the rotatable forming drum 26. The scarfing roll assembly can provide a conventional trimming mechanism for removing any excess, radial thickness of the laid fibrous web that has been deposited on the forming surface 28. The scarfing operation can yield a fibrous web having a selected contour on a major face surface of the fibrous web that has been contacted by the scarfing roll 58. The surface of the scarfing roll can be adjusted to provide a desired contour along the scarfed surface of the fibrous web 40. In the representatively shown arrangement, the scarfing roll can, for example, be configured to provide a substantially flat surface along the scarfed surface of the fibrous web 40. The scarfing roll can optionally be configured to provide a non-flat surface. The scarfing roll 58 is disposed in spaced adjacent relationship to the forming surface, and the forming surface is translated past the scarfing roll. A conventional transporting mechanism, such as a suction fan (not shown) can draw the removed fibrous material away from the formed fibrous web and out from the scarfing chamber 56.

In the representatively shown configuration, the scarfing roll 58 rotates in a direction which moves a contacting surface of the scarfing roll in a counter-direction that is opposite the movement direction of the laid fibrous web 40. Alternatively, the scarfing roll 58 may be rotated to provide a co-directional movement of the roller surface relative to the surface of the forming drum most proximate thereto. In either situation, the rotational speed of the scarfing roll 58 should be suitably selected to provide an effective scarfing action against the contacted surface of the formed fibrous web. In like manner, any other suitable trimming mechanism may be employed in place of the scarfing roll assembly to provide a cutting or abrading action to the laid fibrous web by a relative movement between the fibrous web 40 and the selected trimming mechanism.

After the scarfing operation, the airlaid fibrous web can be moved to an optional pressure blow-off zone 42. In the blow-off zone 42, air can be introduced under pressure and directed radially outwardly against the fibrous web on the portion of the forming surface that becomes aligned with the blow-off zone. The gas pressure can effect a ready release of the fibrous web from the forming surface 28, and the fibrous web 40 can be removed from the forming surface onto a suitable take-off conveyor, such as provided by a system which includes the representatively shown endless conveyor belt 46 disposed about rollers 48. In a particular configuration of the invention, a vacuum suction box 116 can be located below a conveyor belt 46 to help remove the web 40 from the forming surface 28. The vacuum box 116 opens onto the belt 46, and a suction of air out of the vacuum box can draw an air flow through perforations in the conveyor belt. This flow of air can, in turn, operate to draw the web 40 away from the forming surface. The vacuum box can be employed with or without the use of a positive pressure in the blow-off zone 42. The removed fibrous web can provide an interconnected series of pads 50, and each pad can have an selected surface contour which substantially corresponds to the contour provided by the corresponding portions of the forming surface 28 upon which each individual pad was formed.

As representatively shown, the forming surface 28 can be provided along the outer cylindrical surface of the forming drum 26, and can extend along the axial (cross-directional) and circumferential (machine-directional) dimensions of the forming drum. With reference to FIG. 3 and FIGS. 6 through 8A, the structure of the forming surface can be composed of an assembly, and can include a support frame 60 which operatively locates and secures a selected foraminous member 62 to the forming drum 26. The foraminous member may include a screen, a wire mesh, a hard-wire cloth, a perforated member or the like, as well as combinations thereof. In a particular aspect, the foraminous member 62 can include a fluted member having open channels which can extend generally radially and can allow a substantially free flow of air or other selected gas from the outward-side of the drum towards the center of the drum. The flutes or channels can have any desired cross-sectional shape, such as circular, oval, hexagonal, pentagonal, other polygonal shape or the like, as well as combinations thereof. The illustrated configuration of the fluted foraminous member can, for example, have a fluted structure in which the channels are arranged to have a rectangular cross-sectional shape. Such honeycomb structures are well known in the art, and can be composed of various materials, such as plastic, metal, ceramics and the like, as well as combinations thereof. For example, suitable materials and structures are available from INNOVENT, a business having offices located in Peabody, Mass., U.S.A.

In a desired feature of the invention, the radially outward surface of the fluted member or other foraminous member 62 can be configured with a selected surface contour. The contoured surface regions of the foraminous member 62 can be formed to have any operative shape. In desired arrangements, the contour shape can be trapezoidal. Alternatively, the contour shape can be domed or flat.

The surface contour can be formed and distributed along the axial and circumferential dimensions of the foraminous member, and can be configured to have a non-constant, contoured depth. In the shown arrangement, the contoured depth can extend radially into or out of the z-directional thickness of the foraminous member 62, and can be configured to provide a desired variation in thickness of the formed fibrous web 40. In desired arrangements, the variation in the z-directional surface contour can have a selected pattern, and the pattern may be regular or irregular in configuration. For example, the pattern of the surface contour can be configured to substantially provide a selected repeat-pattern along the circumferential dimension of the forming drum. The surface contour of the foraminous member 62 can have one or more regions with a first average depth, and can further have one or more regions with a relatively greater second average depth. Each region with the first average depth can provide a lower-basis-weight region of the forming surface, and each region with the greater second depth can provide a relatively higher-basis-weight region of the forming surface. Desirably, each region with the first average depth can be substantially contiguous with an adjacent region with the greater second depth. Each low-basis-weight region can be employed to form a relatively lower-basis-weight portion or section of the fibrous web 40, and each higher-basis-weight region can be employed to form a relatively higher-basis-weight portion or section of the fibrous web 40. Subsequently, each lower-basis-weight section of the fibrous web can be employed to form a relatively lower-basis-weight section of an individual fibrous pad 50, and each higher-basis-weight section of the fibrous web can be employed to form a relatively lower-basis-weight section of such individual fibrous pad 50.

In a particular feature, the foraminous member 62 can have a z-directional contour pattern which is substantially free of compound curvatures. For example, the contour pattern of the foraminous member 62 can be configured to have a z-directional contour which varies depth-wise along the longitudinal direction 34. Additionally, the z-directional contour pattern along the surface of the foraminous member 62 can provide a substantially constant depth with respect to the lateral cross-direction 36.

Another aspect of the invention can include a perforated plate member 64 which is arranged superjacent the foraminous member 62 and positioned relatively outboard from the fluted member. As representatively shown, the plate member 64 can have a shape or surface contour which substantially matches and corresponds to the surface contour of the foraminous member 62. The perforated plate member can desirably be relatively thin, and in particular arrangements, the thickness of the plate member can be within the range of about 0.005–0.030 inch (about 0.012–0.076 cm). In desired arrangements, the perforated plate member 64 can provide a separation between the foraminous member 62 and the formed web 40. Additionally, the plate member can help provide a surface that can readily release the web 40 when a separation of the web from the forming drum is desired.

The perforations in the plate member 64 can be arranged in any operative, regular or irregular pattern, and the perforations may have any operative shape. For example, the perforations may be configured with a substantially 90° square pattern or a substantially 60° hexagonal pattern. Additionally, the perforations may have any operative size. For example, the perforations may be generally circular, and may have diameters within the range of about 0.009–0.04 inch (about 0.23–1 mm).

In a further aspect, one or more non-flow regions of the forming drum surface may be operatively formed by employing any suitable blocking mechanism that can cover or otherwise occlude the flow of gas through selected regions of the forming surface. As a result, the blocking mechanism can deflect or reduce the amount of fibers deposited on the areas of the forming surface that are covered by the blocking mechanism. The blocking mechanism can optionally be configured to form other desired elements, such as a series of key notches 92 on the laid fibrous web 40. The key notches can, for example, provide sensing point for locating and positioning a subsequent severing of the longitudinally extending fibrous web into discrete fibrous pads 50 (e.g. FIGS. 13 and 14).

With reference to FIGS. 1, 3 and 5, the forming surface 28 can have disposed thereon at least one side-masking member 52. Desirably, the invention can include a cooperating system side-masking members 52 and 54. In the representatively shown configuration, the side-masking members can be provided by a pair of laterally opposed ring members which extend circumferentially around the forming drum 26. In desired arrangements, the side-masking members can be selectively shaped and contoured, and can be configured to provide opposed, symmetrically arranged contour rings. Each of the contour rings can have a cross-directional extent that is varied in a selected pattern to provide a laterally varying, inboard side contour. In particular arrangements the side contours in the first and second ring members can be substantial mirror-images of each other. In another feature, at least one ring member, can include one or more key tabs 78. The individual key tabs may, for example, be employed for marking or otherwise identifying each intended article length along the circumference of the forming drum. Such contour rings can be particularly advantageous when the forming drum system is employed to produce absorbent pads for use in disposable, shaped absorbent articles, such as diapers, children's training pants, feminine care products, adult incontinence products and the like. The contour rings or other side-masking members can be configured to substantially prevent a deposition of fibers in selected regions along the side margins of the forming surface 28 to thereby form corresponding arcuate, cut-out sections along the side regions of the airlaid fibrous web 40.

The side walls 70 and 72 can have a substantially straight configuration along the machine direction 34 to produce a substantially rectangular, ribbon shaped fibrous web 40 (e.g. FIGS. 4, 7 and 7A). In other desired arrangements, the inboard side walls 70 and 72 of the ring members 52 and 54 can be contoured along the cross-direction 36 (e.g. FIGS. 1, 6 and 6A). In the representatively shown arrangement, the side walls of the contoured ring members can have a serpentine, undulating contour along the cross-direction 36. Additionally, the first and second contour rings 52 and 54 can be cooperatively arranged and configured to provide alternating, narrow and wider regions of the forming surface 28.

The present invention can incorporate a selected gap or spacing 88 along the cross-direction between the laterally inboard side walls 70 and 72 of the ring members 52 and 54. For example, in the appointed narrow, crotch regions of the forming surface 28, the spacing 88 can be at least a minimum of about 2 cm (about 0.75 inch). The crotch spacing can alternatively be at least about 2.5 cm and optionally can be at least about 3 cm (about 1.2 inch) to provide desired benefits. In a further aspect, the crotch spacing can be not more than about 30 cm (about 11.8 inch). The crotch spacing can alternatively be not more than about 25 cm, and optionally can be not more than about 20 cm (about 7.9 inch) to provide improved benefits. If the crotch spacing is outside the indicated limits, the pads formed from the fibrous web may not provide the desired combinations of absorbency, fit and comfort.

The cross-directional width of the foraminous member 62 is significantly greater than the cross-directional spacing or gap between the first ring member 52 and the second ring member 54. As a result, the method and apparatus of the invention can be more readily adjusted to provide different cross-directional dimensions in the fibrous web 40. An optional cross-directional filler plate or end-masking member 80 can be employed to help form discrete, individual pads 50. And to adjust the longitudinal dimension of the individual pads 50.

The first side-masking, ring member 52 can desirably have a bottom surface profile or surface contour which substantially matches a correspondingly adjacent surface profile or surface contour of the foraminous member 62. Similarly, the second side-masking, ring member 54 can desirably have a bottom surface profile which substantially matches a correspondingly adjacent surface profile of the foraminous member 62.

Additionally, the inboard side wall surfaces 70 and 72 can be substantially non-foraminous, and operatively resistant to the passage of gas therethrough. As a result, the inboard side walls 70 and 72 can be substantially impermeable to the gas flow generated by the method and apparatus of the invention. The inboard side wall surfaces 70 and 72 can substantially prevent an excessive lateral movement of air, and the airflow through the forming surface 28 can be better directed in a desired radial or z-direction 35. As a result, the invention can more effectively direct the air-entrained fibers and superabsorbent particles in a substantially radial direction onto the forming surface 28. The removal of vacuum from the side walls 70 and 72 can also help improve the ability to release the fibrous web 40 from the forming surface 28.

The application of engineered coatings onto the inboard side wall surfaces 70 and 72 can also help improve the releasing of the fibrous web 40 from the forming surface 28. The engineered coatings can be configured to provide selected properties, such as smoothness, low friction, and high durability. Examples of desired engineered, coating materials can include HARDLUBE material, NORKOTE material, coating materials that include polytetrafluoroethylene or other low-friction material; and the like, as well as combinations thereof. The HARDLUBE and NORKOTE materials are available from Pioneer Metal Finishing Inc., a business having offices located in Green Bay, Wis.

In another aspect, the first and/or second side walls 70 and 72 can have a selected wall angle (e.g. FIG. 8A). The first inboard side wall surface 70 can have a wall angle 82 which is not more than a maximum of about 90°. In another aspect, the first inboard side wall surface 70 can have a wall angle which is not less than a minimum of about 75°. Similarly, the second inboard side wall surface 72 can have a wall angle 82 which is not more than a maximum of about 90°. The second inboard side wall surface 72 can further have a wall angle which is not less than a minimum of about 75°.

The side wall angles employed with the present invention can reduce an undesired funneling of fibers and particles toward the cross-directional center of the forming surface 28, and can help reduce an undesired ricocheting of particles off from the forming surface. The various aspects and features of the side walls 70 and 72 can reduce any non-radial airflows and can provide a more uniform distribution of superabsorbent material and fibers along the cross-direction of the fibrous web 40.

For example, when the side wall angle 82 is less than about 75°, the resulting non-radial components of airflow can increase the ricocheting effect of the superabsorbent material and can undesirably funnel the superabsorbent material toward the cross-directional center of the forming surface 28. This can create an undesired, excessive basis weight gradient across the cross-directional width of the fibrous web 40.

During a debulking process, where the fibrous web 40 or the formed pad 50 is compressed to a desired thickness and density, the fibrous web or pad can squeeze out to a larger width as they are compressed. When employing conventional forming screens, with tapered sidewall pockets, the formed web or pads have spread or grown. This web or pad growth has been undesirable, because it has tended to cause a concentration of the superabsorbent into a narrow stripe along the middle portion of the web or pad. To compensate for the web or pad growth, conventional manufacturing processes have incorporated a narrower pocket design with decreased cross-directional width. The narrower pocket design, however, can direct even more particles of superabsorbent material into the center of the formed web, resulting in an undesired further concentration of the superabsorbent along the middle portion of the web or pad.

In contrast to such conventional arrangements, the configuration of the present invention can help reduce the excessive spread and growth of the web or pad during compressing and densification. In particular, the configuration of the sidewalls 70 and 72 can help reduce the undesired growth and spreading.

The forming surface 28 can include a frame 60 which operatively configured to position and hold the foraminous member 62 on the forming drum 26. The foraminous member 62 is disposed on the frame 60, and the perforated plate member 64 may be arranged to overlie the foraminous member 62. The side-masking members 52 and 54 are secured over the perforated plate member 64. With reference to FIGS. 6 through 8, the foraminous member 62 can be configured to extend laterally past and beyond the first and second, inboard side wall surfaces 70 and 72 of the side-masking members 52 and 54, respectively. Beneath the forming surface 28, the forming drum 26 can include a generally cylindrical sealing ring member 44 having a plurality of perforations or openings formed therethrough. The perforations can allow a substantially free passage of air along the radial direction of the drum, and may be arranged across the sealing ring surface in a regular or irregular array, as desired.

In a particular aspect, the method and apparatus of the invention can further include a first side-cover member 84 which is operatively attached and positioned along a first, laterally outboard edge region of the foraminous member 62. Similarly, a second side-cover member 86 can be operatively attached and positioned along a second, laterally outboard edge region of the foraminous member 62. In the representatively shown arrangement, for example, the first and second side-cover members 84 and 86 can be operatively attached to the forming surface frame 60.

As representatively shown, the side-cover members can be joined to the forming surface frame 60 by employing conventional attaching or mounting mechanisms. Additionally, the frame 60 can include side flanges 90 which can provide suitable mounting members for operatively securing the frame to the circumferential periphery of the forming drum 28.

Another feature of the invention can provide at least one end-masking member 80 which is interposed between the first and second side-masking members 52 and 54, respectively. In a particular aspect, the filler plate or end-masking member 80 can be configured to have an adjustable length along the machine-direction 34. The adjustable filler plate can help can be configured to extend into the lower-basis-weight section 110 of the foraminous member section 162 provide a selected shifting of the higher-basis-weight section of the formed fibrous web 40 along the machine-direction of the individual absorbent pad 50. Alternatively, the filler plate 80 can be configured to extend into the higher-basis-weight section 112 of the foraminous member section 162 to adjust the length of the high-basis weight region of the formed fibrous web 40.

Various releasable and adjustable attachment mechanisms may be employed with the present invention. Such releas-able and adjustable attachment mechanisms can, for example, include screws, nuts, bolts, rivets, releasable welds, releasable adhesives, latches, clamps, pins, magnets, wedges, or the like, as well as combinations thereof.

In the shown configuration, the first and second releasable attachment mechanisms can be provided by suitable screws or nuts and bolts which engage cooperating slots formed in the ring members 52 and 54. As representatively shown, the slots are elongated in the transverse cross-direction 36 to accommodate a lateral movement of the ring members 52 and/or 54 relative to the foraminous member 62.

Figure 9:
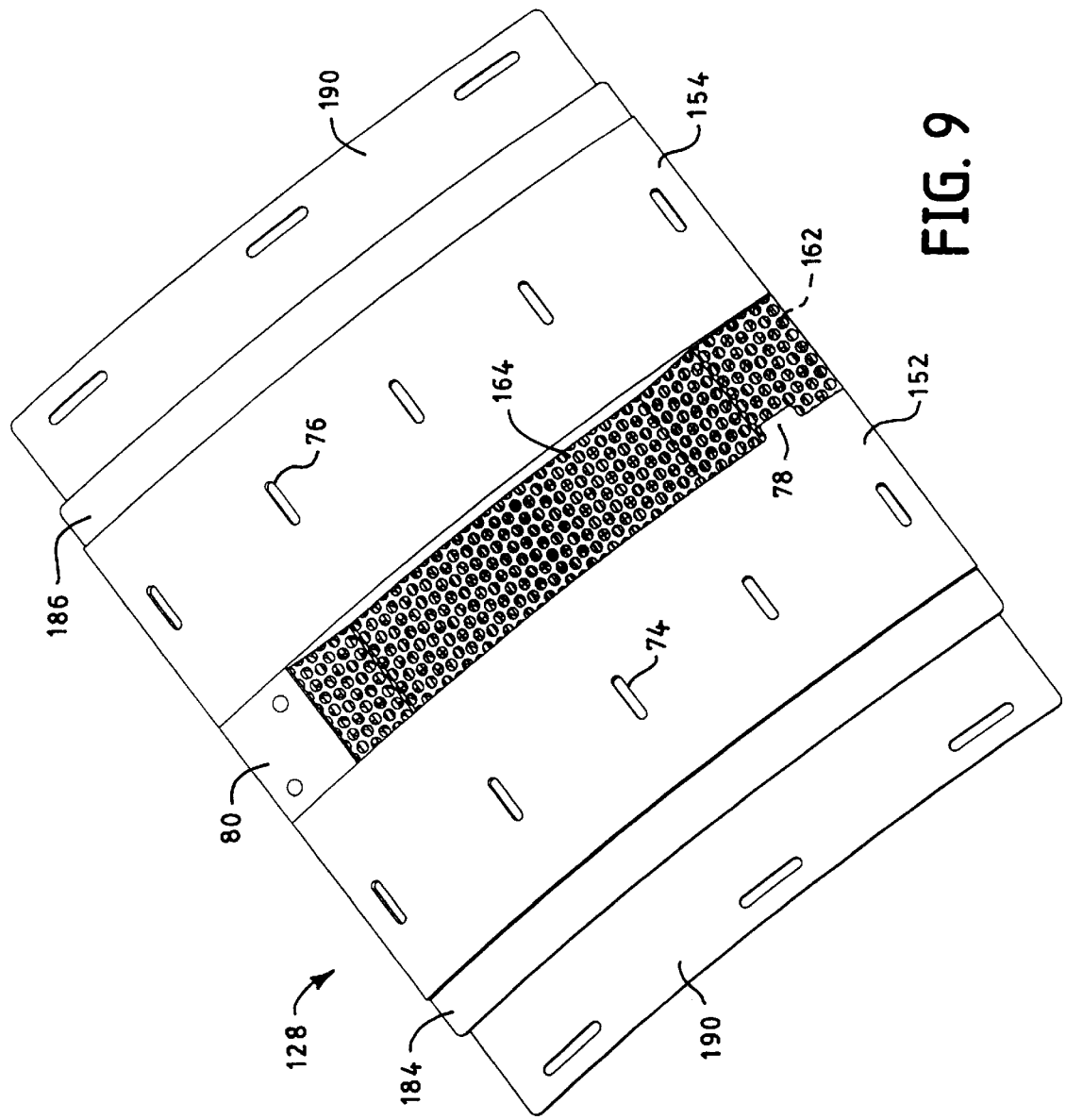
FIG. 9 shows a perspective top view of a representative forming surface section or subassembly that can be employed with the present invention to form a fibrous web that has generally straight side margins, and can be divided into individual pads having a generally rectangular shape.
Figure 10:
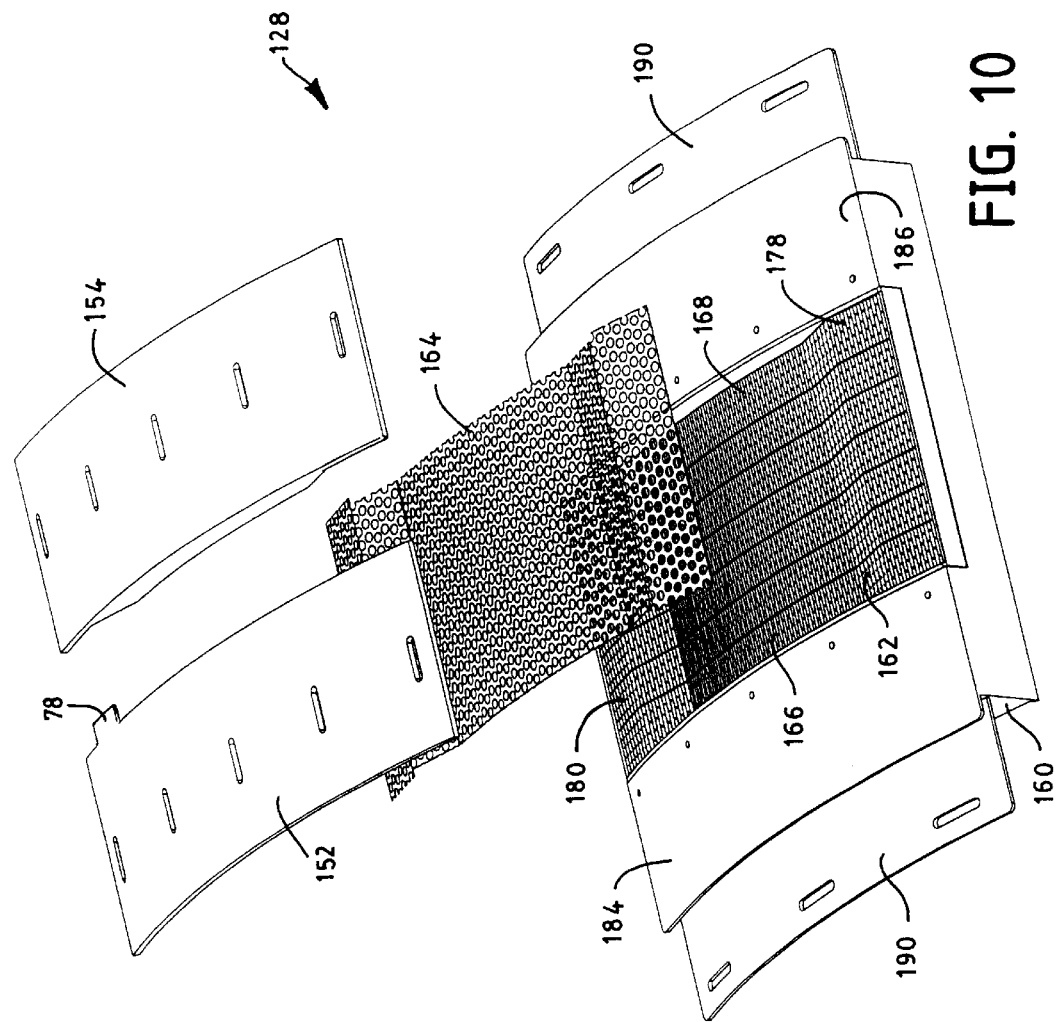
FIG. 10 shows a perspective, expanded view of a representative forming surface section.
Figure 11:
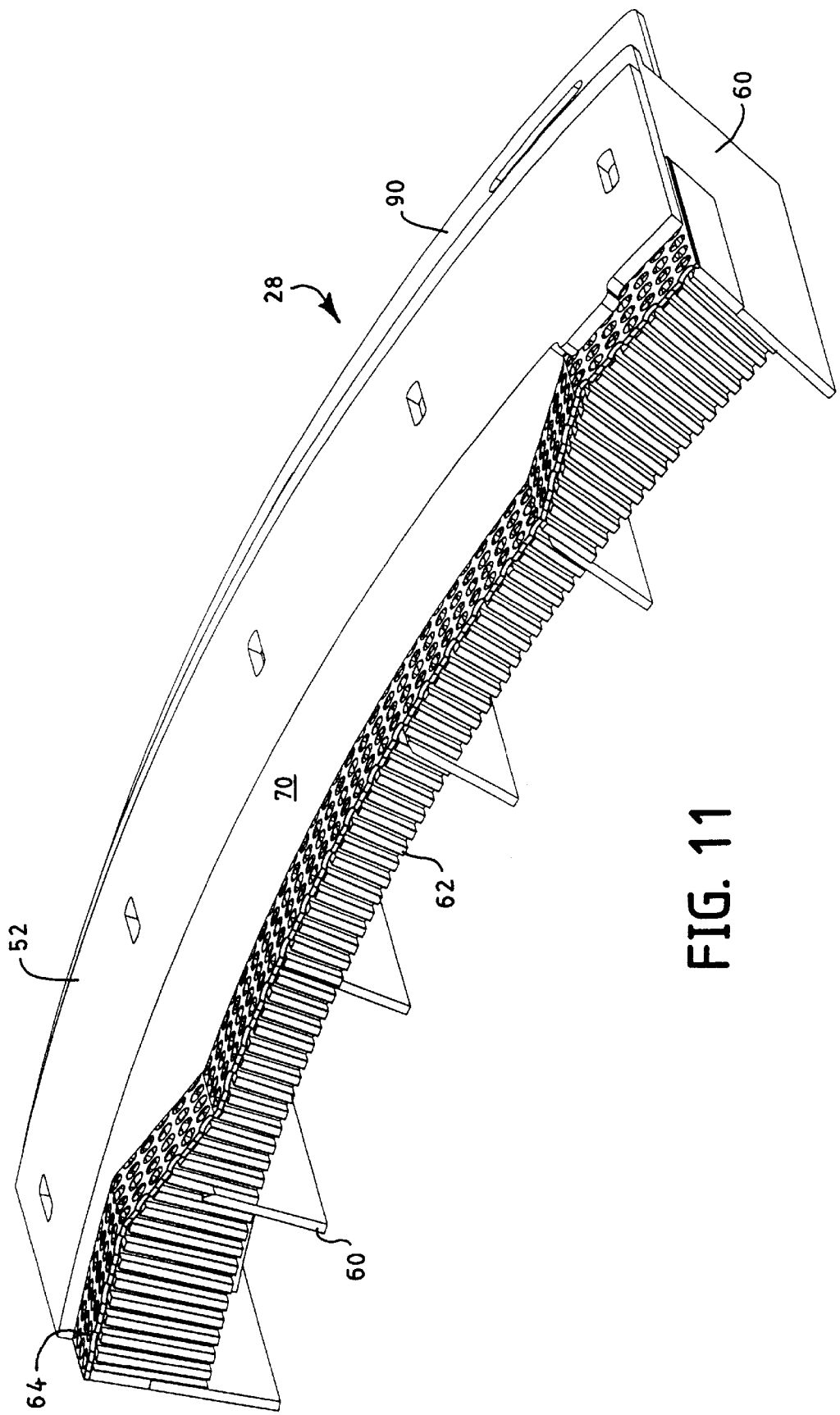
FIG. 11 shows a perspective view of a representative portion of a forming surface which has been sectioned along its longitudinal length.
Figure 12:
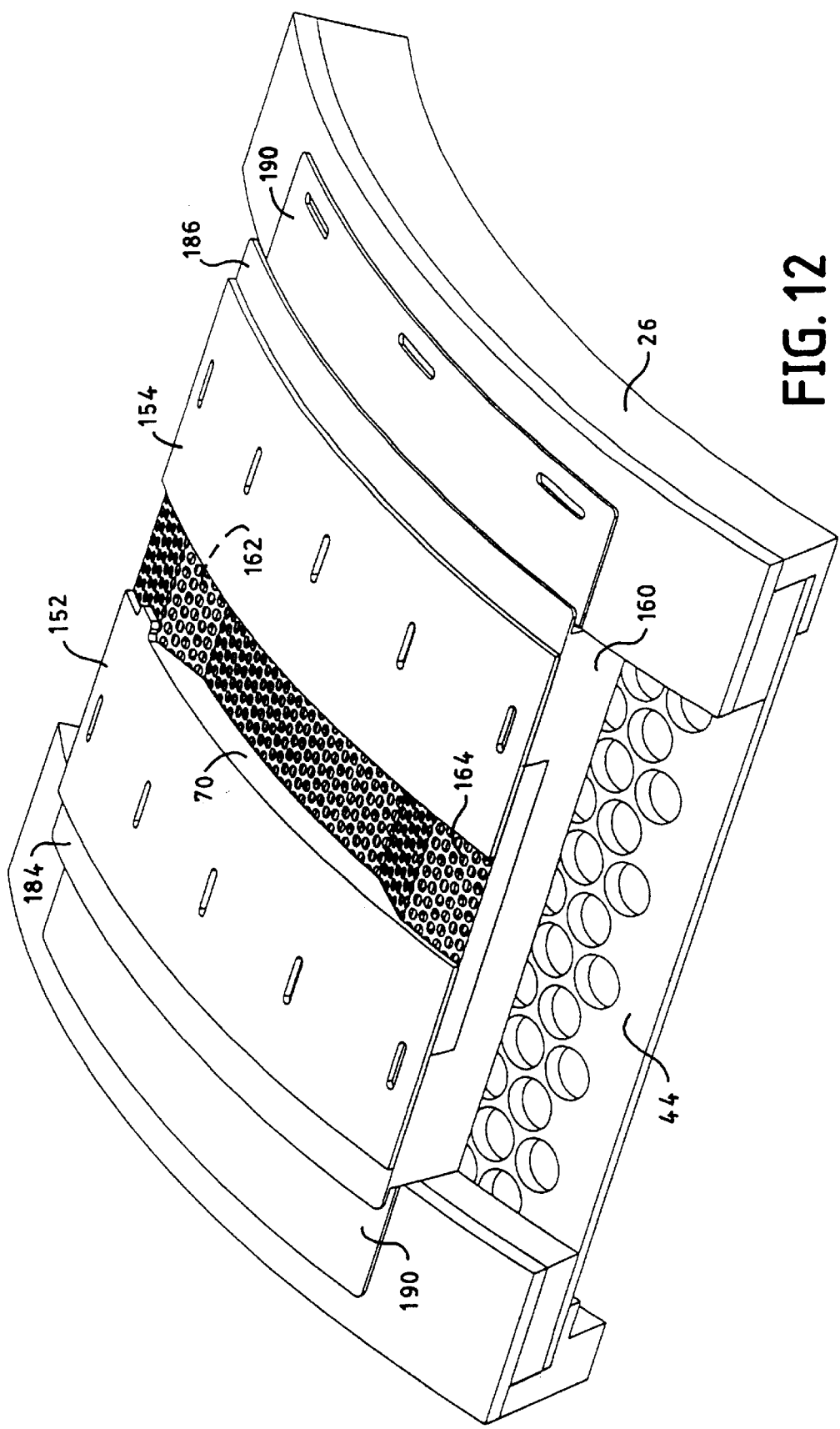
FIG. 12 a perspective view of a representative forming surface section that has been mounted on a forming drum.

In a particular aspect, the foraminous forming surface 28 can include at least one, and desirably, a plurality of forming portions or sections 128 (e.g. FIGS. 9 and 10). Each forming section 128 can provide a subassembly of the overall foraminous forming surface 28, and each forming section can be independently removable and replaceable on the forming drum 26. The multiplicity of forming sections can operatively joined and located in an interconnected series along the outer periphery of the forming drum. Typically, each of the forming portions or sections 128 can substantially correspond to an individual fibrous pad 50 that may eventually be formed from the fibrous web 40.

In another aspect, the foraminous member 62 can include a plurality of foraminous member sections 162, and each of the foraminous member sections can be located in a corresponding portion or section 128 of the forming surface 28. The foraminous member section 162 can have a leading-edge portion 178, a trailing-edge portion 180, a first side portion 166, a laterally opposed second side portion 168, a lower-basis-weight section 110, and a relatively higher-basis-weight section 112 which is contiguous with the low-basis-weight section 110. The lower-basis-weight section 110 can be employed to form a relatively lower-basis-weight portion or section of the fibrous web 40, and the higher-basis-weight section 112 can be employed to form a relatively higher-basis-weight portion or section of the fibrous web 40. Subsequently, a lower-basis-weight section of the fibrous web can be employed to form a relatively lower-basis-weight section of an individual fibrous pad 50, and a higher-basis-weight section of the fibrous web can be employed to form a relatively lower-basis-weight section of the individual fibrous pad 50.

A longitudinally extending, first side-masking member section 152 can be located superjacent the first side portion 166 of the foraminous member section 162, and can have a first inboard side wall surface 70 with a predetermined first contour. The first inboard side wall 70 can have a first contoured edge portion, and can have a least a depth-wise contour with selectively varying, non-constant dimensions along the z-directional thickness direction. Additionally, the first inboard side wall can have a lateral contour with selectively varying, non-constant dimensions along the cross-direction 36. The first side-masking member section 152 is at least laterally movable relative to the foraminous member section 162. Accordingly, the first inboard side wall 70 is also at least laterally movable relative to the foraminous member section 162.

At least a second, separately provided, contoured, longitudinally extending, side-masking member section 154 can be located superjacent the second side portion 168 of the foraminous member section 162, and can have a second inboard side wall surface 72 with a second, predetermined contour. The second inboard side wall 72 can have a first contoured edge portion, and can have a least a depth-wise contour with selectively varying, non-constant dimensions along the z-directional thickness direction. Additionally, the second inboard side wall can have a lateral contour with selectively varying, non-constant dimensions along the cross-direction 36. The second side-masking member section 154 is at least laterally movable relative to the foraminous member section 162. Accordingly, the second inboard side wall 72 is also at least laterally movable relative to the foraminous member section 162. Additionally, the second side-masking member section 154 can be at least laterally movable relative to the first side-masking member 152. A first releasable attachment system 74 can selectively hold at least the first side-masking member section 152 at a substantially fixed position relative to the foraminous member section 162 during a moving of the foraminous member section along the longitudinal, machine-direction 34.

Each of the forming surface sections 128 can include a corresponding frame section 160 which is operatively constructed and arranged to position and hold its associated, component portions and sections of the forming surface. In the representatively shown configuration, each frame section 160 can include an end plate member at either or both of its longitudinal ends. Additionally, each forming section 128 can include corresponding flange sections 190, a corresponding first side cover section 184, and a corresponding second side cover section 186.

Figure 13:
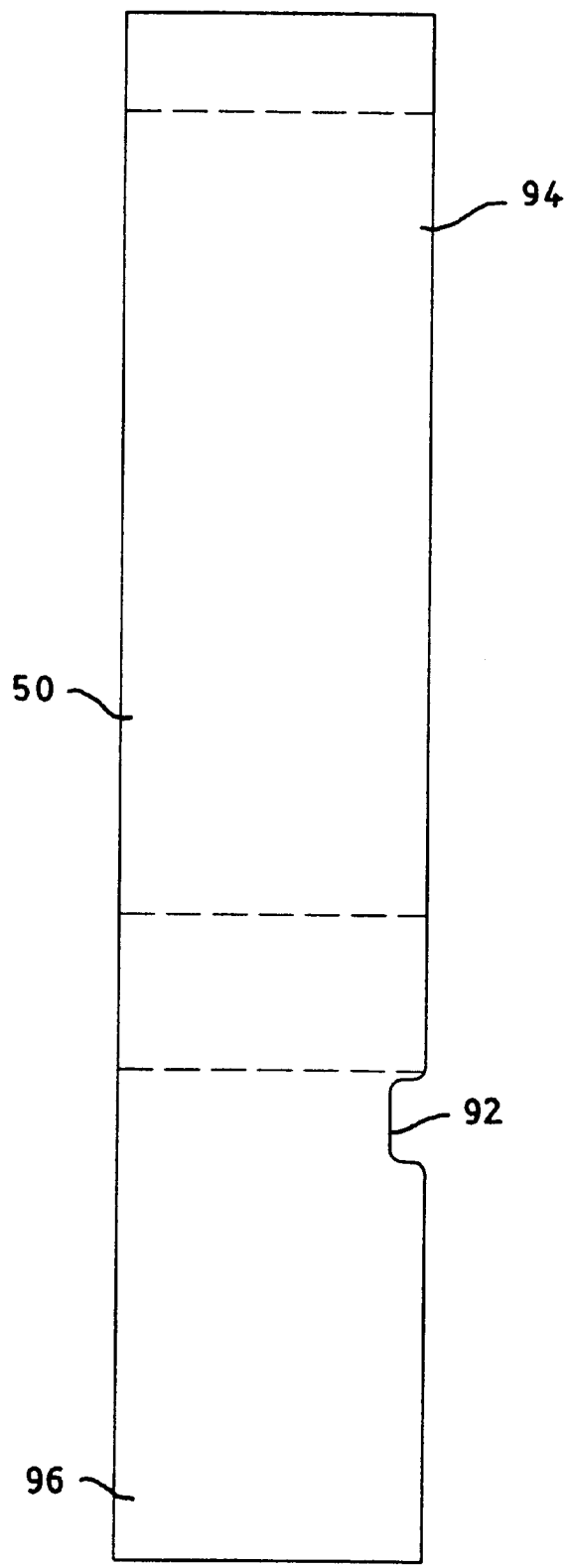
FIG. 13 shows a schematic top view of a representative fibrous web segment which can be formed by employing the method and apparatus of the invention.

FIGS. 13 and 14 show a representative fibrous article, which can be formed by the method and apparatus of the invention. The fibrous article is particularly suitable for use in an absorbent article, such as disposable diaper. The airlaid fibrous web pad 50 can be formed from the longitudinally extending web 40 by appropriately severing the web 40 transversely into suitable lengths. The fibrous pad 50 can have an appointed, article rear section 96, and an appointed, article front section 94. As mentioned previously, this fibrous pad may feature leg cut-outs along its side margins when the invention employs side-masking members 52 and 54 that are configured to provide contour rings. The key notch 92 can be formed at a selected side edge of each fibrous pad article, and the notch or "key" can be employed as a reference point for severing the longitudinally extending fibrous web into lengths of predetermined dimension.

A longitudinal first region of the fibrous pad 50, such as provided by the pad front section 94, can provide a higher basis weight region of the article relative to a second, lower basis weight region of the pad, such as provided by the rear pad section 96. Where the fibrous pad has shaped, leg cut-outs, the pad may include laterally extending corner segments or "ears". The pad 50 includes a relatively low-basis-weight region and a contiguous, relatively high-basis-weight region. The high-basis-weight region can substantially correspond to a non-separable protrusion from a first surface of the fibrous pad that corresponds to the concavely contoured surface portion of the forming surface 28. The pad 50 can feature a second major surface which can be substantially flat, and can typically correspond to the surface processed by the scarfing roll 58. The pad side surfaces correspond to the side walls provided by side-masking members 52 and 54. The end surfaces of the pad can correspond to severed edges, or may correspond to the transverse and depth-wise extending, end wall surfaces provided by one or more endmasking members 80.

The method and apparatus of the invention can be configured to produce a relatively high basis weight region that extends transversely across substantially the entire cross-directional width of its corresponding portion of the fibrous pad 50. Similarly, the invention can be configured to produce a relatively low basis weight region that extends transversely across substantially the entire cross-directional width of its corresponding portion of the fibrous pad.

In another aspect, the method and apparatus of the invention can be configured to include a foraminous member 62 having at least one formed pocket or depression region. In an optional feature, the foraminous member 62 with one or more of the pocket or depression regions may be employed to produce a higher-basis-weight region that has a basis weight variation or change with respect to the cross-directional width of its corresponding portion of the fibrous web 40 or pad 50. As representatively shown in FIGS. 15 and 15A, for example, the invention can be configured to include a foraminous member 62 having at least one formed pocket or depression region 98. In a particular feature, the pocket region 98 can assist in the production of the higher-basis-weight region of the formed web or pad. In an optional feature, the pocket region can help provide a fibrous basis weight that is nonuniform along the cross-direction of the formed web or pad. In the illustrated arrangement, a medial portion of one or more of the appointed, higher-basis-weight sections 112 of the foraminous member 62 can be machined or otherwise formed with a corresponding pocket depression region 98. Similarly, the perforated plate member 64 can be suitably formed and shaped to substantially match and operatively conform to the surface contours of the pocket depression region. As representatively shown, the method and apparatus can provide a forming geometry or configuration that includes a first portion having a first geometry with substantially non-foraminous sidewalls, and a supplemental portion having a second geometry with foraminous sidewalls. The foraminous sidewalls may be substantially vertical or may be slanted at an operative angle to facilitate the release of the formed fibrous web 40 from the foraminous member 62 and the forming surface.

It has been known that conventional geometries with tapered, foraminous sidewalls have tended to fill with fibers first along a perimeter region where the sidewalls meet the relatively deepest portion of the forming surface. As a result, any deficiency in fiber filling typically occurs in the center region of the formed web. It has been observed that the forming structures with the solid, substantially non-foraminous sidewalls tend to first fill with fibers at the middle region of the formed web, and that any deficiency in fiber filling is at the perimeter region. Accordingly, a combination of the two sidewall configurations may help to provide an improved airflow balance at the perimeter and center regions of the formed web. As a result, the apparatus and method of the present invention may help to provide a more uniform distribution of fiber basis weight across the higher-basis-weight regions of the formed web.

It will be readily apparent that various conventional devices and techniques can be employed to sever fibrous web 40 into predetermined lengths to provide selected laid fibrous articles. For example, the longitudinally extending fibrous web 40 can be transferred from the take-off conveyor 46 to a transverse severing system. The severing system may, for example, include a die cutter, a water cutter, a rotary knives, reciprocating knives or the like, as well as combinations thereof. A mechanical or electronic sensor mechanism can detect the key notches 92 within the web 40 and the severing system can operate an actuator which operatively moves a cutting member against selected regions of web 40, thereby transversely severing the web into discrete articles, such as the pads 50. After severing, the discrete fibrous pads 50 can be transported and delivered for further processing operations, as desired. In another aspect of the invention, the discrete fibrous articles 50 can be directly formed on forming surface 28. As representatively shown in FIGS. 4 and 9, a plurality of the blocking end-masking members 80 can be located at selected locations along the circumference of the forming surface. End-masking members 80 interconnect between side-masking members 52 and 54 and extend along the axial and circumferential dimensions of the forming drum 26. These end-masking members also overlie the forming surface 28 and can block the accumulation of fibers along relatively narrow, transverse portions of the forming surface. As a result, the deposition of fibers onto forming surface 28 can create a substantially non-continuous web included of individual, discrete fibrous articles, such as the discrete pads 50.

In the various attachments and securements employed in the constructions of the method and apparatus of the invention, it should be readily apparent that any conventional attachment or securement technique may be employed. Such techniques may, for example, include adhesives, welds, screws, bolts, rivets, pins, latches, clamps or the like, as well as combinations thereof.

Similarly, it should be readily apparent that any conventional material may be employed to construct the various components incorporated into the method and apparatus of the invention. Such materials can include synthetic polymers, fiberglass-resin composites, carbon fiber-resin composites, metallic composites, ceramic composites, and the like, as well as combinations thereof. The materials are typically selected to provide desired levels of strength, durability, ease of manufacture, and ease of maintenance.

Although various illustrative and representative configurations have been described in detail herein, it is to be appreciated that other variants, modifications and arrangements are possible. All of such variations, modifications and arrangements are to be considered as being within the scope of the present invention.

We claim:

1. An apparatus for forming an airlaid fibrous web on a moving surface, said apparatus having a longitudinal direction, a lateral cross-direction and a depth-wise z-direction, and said apparatus comprising:

a contoured foraminous member having a first side portion, a laterally opposed second side portion, and a depth contour formed into a thickness of said foraminous member, said depth contour having a lower-basis-weight section, and a higher-basis-weight section which is contiguous with said low-basis-weight section;

a longitudinally extending, first side-masking member which is located superjacent said first side portion of the foraminous member, has a first inboard side wall surface, and is at least laterally movable relative to said foraminous member;

at least a second, separately provided, longitudinally extending, side-masking member which is located superjacent said second side portion of the foraminous member, has a second inboard side wall surface, and is at least laterally movable relative to said foraminous member; and a first releasable attachment system for selectively holding at least said first side-masking member at a substantially fixed position relative to said foraminous member during a moving of said foraminous member along said longitudinal direction, wherein said first side-masking member has a bottom surface profile along said longitudinal direction;

said bottom surface profile provides a depth-wise contour with varying, non-constant dimensions along a z-directional thickness direction; and said bottom surface profile of said first side-masking member substantially matches a correspondingly adjacent surface profile of said foraminous member in said low-basis-weight and high-basis-weight sections of the foraminous member.

2. An apparatus as recited in claim 1, further including a second releasable attachment system for selectively holding said second side-masking member at a substantially fixed position relative to said foraminous member during the moving of said foraminous member along said longitudinal direction.

3. An apparatus as recited in claim 1, wherein said moving surface is provided by a peripheral surface region of a rotatable forming drum.

4. An apparatus as recited in claim 1, wherein said contoured foraminous member has a contour pattern which is substantially free of compound curvatures.

5. An apparatus as recited in claim 1, further comprising at least one end-masking member which is interposed between said first and second side-masking members.

6. An apparatus as recited in claim 1, wherein said first inboard side wall surface has a wall angle of not more than a maximum of about 90 degrees.

7. An apparatus as recited in claim 6, wherein said first inboard side wall surface has a wall angle of not less than a minimum of about 75 degrees.

8. An apparatus as recited in claim 1, wherein said second inboard side wall surface has a wall angle of not more than a maximum of about 90 degrees.

9. An apparatus as recited in claim 8, wherein said second inboard side wall surface has a wall angle of not less than a minimum of about 75 degrees.

10. An apparatus as recited in claim 1, wherein said foraminous member extends laterally beyond said first and second, inboard side wall surfaces.

11. An apparatus as recited in claim 1, wherein said second side-masking member has a bottom surface profile along said longitudinal direction; said bottom surface profile of said second side-masking member provides a depth-wise contour with varying, non-constant dimensions along said z-directional thickness direction; and said bottom surface profile of said second side-masking member substantially matches a correspondingly adjacent surface profile of said foraminous member in said low-basis-weight and high-basis-weight sections of the foraminous member.

12. An apparatus as recited in claim 1, further comprising a first side-cover member which is operatively attached to said apparatus and is positioned along a first, laterally outboard edge region of said foraminous member.

13. An apparatus as recited in claim 12, further comprising a second side-cover member which is operatively attached to said apparatus and is positioned along a second, laterally outboard edge region of said foraminous member.

14. An apparatus for forming an airlaid fibrous web on a moving surface, said apparatus having a longitudinal direction, a lateral cross-direction and a depth-wise z-direction, and said apparatus comprising:

a contoured foraminous member section having a leading-edge portion, a trailing-edge portion, a first side portion, a laterally opposed second side portion, a lower-basis-weight section, and a higher-basis-weight section which is contiguous with said low-basis-weight section;

a longitudinally extending, first side-masking member section which is located superjacent said first: side portion of the foraminous member, has a first inboard side wall surface with a first contoured edge portion, and is at least laterally movable relative to said foraminous member;

at least a second, separately provided, contoured, longitudinally extending, side-masking member section which is located superjacent said second side portion of the foraminous member section, has a second inboard side wall surface with a second, contoured edge portion, and is at least laterally movable relative to said foraminous member section; and a first releasable attachment system for selectively holding at least said first side-masking member section at a substantially fixed position relative to said foraminous member section during a moving of said foraminous member section along said longitudinal direction; wherein said first side-masking member has a bottom surface profile along said longitudinal direction;

said bottom surface profile provides a depth-wise contour with varying, non-constant dimensions along a z-directional thickness direction; and said bottom surface profile of said first side-masking member substantially matches a correspondingly adjacent surface profile of said foraminous member in said low-basis-weight and high-basis-weight sections of the foraminous member.

15. A method for forming an airlaid fibrous web on a moving surface, said method having a longitudinal direction, a lateral cross-direction and a depth-wise z-direction, said method comprising:

a longitudinal moving of a contoured foraminous member having a first side portion, a laterally opposed second side portion, and a depth contour formed into a thickness of said foraminous member;

a locating of a longitudinally extending, first side-masking member at a position which is superjacent said first side portion of the foraminous member, said first side-masking member having a first inboard side wall surface, and said first side-masking member being at least laterally movable relative to said foraminous member;

a locating of at least a second, separately provided, longitudinally extending, side-masking member at a position which is superjacent said second side portion of the foraminous member, said second side-masking member having a second inboard side wall surface, and said second side-masking member being at least laterally movable relative to said foraminous member and relative to said first side-masking member;

a selective holding of said first and second side-masking members with a releasable attachment system at substantially fixed positions relative to said foraminous member during said longitudinal moving of said foraminous member;

a providing of said first side-masking member with a bottom surface profile along said longitudinal direction;

a providing of said bottom surface profile with a depth-wise contour having varying, non-constant dimensions along a z-directional thickness direction; and substantially matching said bottom surface profile of said first side-masking member to a correspondingly adjacent surface profile of said foraminous member in said low-basis-weight and high-basis-weight sections of the foraminous member.

16. A method as recited in claim 15, further comprising a configuring of said foraminous member to include at least one contoured foraminous member section having a leading-edge portion, a trailing-edge portion, a first side portion, a laterally opposed second side portion, a low-basis-weight section, and a high-basis-weight section which is contiguous with said low-basis-weight section;

a configuring of said first side-masking member to include a contoured, longitudinally extending, first side-masking member section located at a position which is superjacent said first side portion of the foraminous member section, said first side-masking member section having a first inboard side wall surface, and said first side-masking member section being at least laterally movable relative to said foraminous member section;

a configuring of said second side-masking member to include at least a second, separately provided, contoured, longitudinally extending, side-masking member section located at a position which is superjacent said second side portion of the foraminous member section, said second side-masking member section having a second inboard side wall surface, and said second side-masking member section being at least laterally movable relative to said foraminous member section and relative to said first side-masking member section;

a configuring of said releasable attachment system to provide a selective holding of said first and second masking members sections at substantially fixed positions relative to said foraminous member section during said longitudinal moving of said foraminous member section;

a providing of said first side-masking member section with a bottom surface profile, along said longitudinal direction;

a providing of said bottom surface profile of the first side-masking member section with a depth-wise contour having varying, non-constant dimensions along the z-directional thickness direction;

substantially matching said bottom surface profile of the first side-masking member section with a correspondingly adjacent surface profile of said foraminous member section in said low-basis-weight and high-basis-weight sections of the foraminous member section;

a providing of said second side-masking member section with a bottom surface profile, along said longitudinal direction;

a providing of said bottom surface profile of the second side-masking member section with a depth-wise contour having varying, non-constant dimensions along the z-directional thickness direction; and substantially matching said bottom surface profile of the second side-masking member section with a correspondingly adjacent surface profile of said foraminous member section, along said longitudinal direction, in said low-basis-weight and high-basis-weight sections of the foraminous member section.

17. A method as recited in claim 15, further comprising an interposing of at least one, separately provided, end-masking member between said first and second side-masking members.

18. A method as recited in claim 15, further comprising an extending of said foraminous member to extend laterally beyond said first and second side wall surfaces.

19. A method as recited in claim 15, wherein a first side-cover member has been operatively attached along a first, laterally outboard edge region of said foraminous member.

20. A method as recited in claim 19, further including an operative attaching of a second side-cover member along a second, laterally outboard edge region of said foraminous member.

21. An apparatus for forming an airlaid fibrous web on a moving surface, said apparatus having a longitudinal direction, a lateral cross-direction and a depth-wise z-direction, and said apparatus comprising:

a contoured foraminous member having a first side portion, a laterally opposed second side portion, and a depth contour formed into a thickness of said foraminous member, said depth contour having a lower-basis-weight section, and a higher-basis-weight section which is contiguous with said low-basis-weight section;

a longitudinally extending, first side-masking member which
  is located superjacent said first side portion of the foraminous member,
  has a first inboard side wall surface,
  is at least laterally movable relative to said foraminous member, and
  has a bottom surface profile along said longitudinal direction,
    said bottom surface profile having a depth-wise contour with varying, non-constant dimensions along a z-directional thickness direction, and
    said bottom surface profile substantially matching a correspondingly adjacent surface profile of said foraminous member in said low-basis-weight and high-basis-weight sections of the foraminous member;

at least a second, separately provided, longitudinally extending, side-masking member which
  is located superjacent said second side portion of the foraminous member,
  has a second inboard side wall surface,
  is at least laterally movable relative to said foraminous member, and
  has a bottom surface profile, along said longitudinal direction,
    said bottom surface profile of the second side-masking member having a depth-wise contour with varying, non-constant dimensions along a z-directional thickness direction, and
    said bottom surface profile of the second side-masking member substantially matching a correspondingly adjacent surface profile of said foraminous member in said low-basis-weight and high-basis-weight sections of the foraminous member; and a first releasable attachment system for selectively holding at least said first side-masking member at a substantially fixed position relative to said foraminous member during a moving of said foraminous member along said longitudinal direction; wherein said first and second side-masking members respectively provide first and second non-foraminous side walls located within said high-basis-weight pocket region of said foraminous member.

* * * * *